(12) United States Patent
Lennon et al.

(10) Patent No.: US 11,840,681 B2
(45) Date of Patent: Dec. 12, 2023

(54) GUT BIOREACTOR AND METHODS FOR MAKING THE SAME

(71) Applicant: THE TRUSTEES OF INDIANA UNIVERSITY, Indianapolis, IN (US)

(72) Inventors: Jay T. Lennon, Bloomington, IN (US); Louis Alexandre van der Elst, Bloomington, IN (US); Emmi Mueller, Bloomington, IN (US); Alexander Gumennik, Bloomington, IN (US)

(73) Assignee: THE TRUSTEES OF INDIANA UNIVERSITY, Indianapolis, IN (US)

( * ) Notice: Subject to any disclaimer, the term of this patent is extended or adjusted under 35 U.S.C. 154(b) by 200 days.

(21) Appl. No.: 17/238,833

(22) Filed: Apr. 23, 2021

(65) Prior Publication Data

US 2021/0332314 A1  Oct. 28, 2021

Related U.S. Application Data

(60) Provisional application No. 63/014,430, filed on Apr. 23, 2020.

(51) Int. Cl.
*C12M 1/12* (2006.01)
*B33Y 10/00* (2015.01)
*B33Y 70/10* (2020.01)
*B33Y 80/00* (2015.01)

(52) U.S. Cl.
CPC ............. *C12M 23/06* (2013.01); *B33Y 10/00* (2014.12); *B33Y 70/10* (2020.01); *B33Y 80/00* (2014.12)

(58) Field of Classification Search
CPC .......... B33Y 10/00; B33Y 70/10; B33Y 80/00; C12M 23/20; C12M 23/34; C12M 23/02
See application file for complete search history.

(56) References Cited

U.S. PATENT DOCUMENTS

| | | | |
|---|---|---|---|
| 3,710,789 A * | 1/1973 | Ersek | A61B 17/8085 606/907 |
| 10,338,000 B2 | 7/2019 | Gumennik et al. | |
| 2010/0316088 A1 | 12/2010 | Bayindir et al. | |
| 2017/0036398 A1 | 2/2017 | Gumennik et al. | |
| 2021/0330864 A1 | 10/2021 | Gumennik et al. | |
| 2021/0333131 A1 | 10/2021 | Gumennik et al. | |

OTHER PUBLICATIONS

Allison, S. D., "Cheaters, diffusion and nutrients constrain decomposition by microbial enzymes in spatially structured environments," 2005, Ecology Letters, 8 pp. 626-635.

Arcidacono, S., et al., "The current state and future direction of DoD gut microbiome research: a summary of the first DoD gut microbiome informational meeting," 2018, Standards in Genomic Sciences, 13 pp. 5.

(Continued)

*Primary Examiner* — Rick K Chang
(74) *Attorney, Agent, or Firm* — Barnes & Thornburg LLP

(57) ABSTRACT

A gut bioreactor includes a fold region and a flow region. The fold regions include members that cooperate to form crypts. The members may have protuberances extending from a surface of the members into the crypts. The gut bioreactors may include multimaterial fibers that are configured to detect aspects of the crypts or may mechanically move portions of the gut bioreactor.

14 Claims, 15 Drawing Sheets

(56) References Cited

OTHER PUBLICATIONS

Arnoldini, M., Cremer, J., and Hwa, T., "Bacterial growth, flow, and mixing shape human gut microbiota density and composition," 2018, Gut Microbes, 9 pp. 559-566.
Aron-Wisnewsky, J., and Clement, K., "The gut microbiome, diet, and links to cardiometabolic and chronic disorders," 2016, Nature Reviews Nephrology, 12 pp. 169-181.
Bein, A., et al., "Microfluidic organ-on-a-chip models of human intestine," 2018, Cellular and Molecular Gastroenterology and Hepatology, 5(4) pp. 659-668.
Bohm, A., Kleessen, B., and Henle, T., "Effect of dry heated inulin on selected intestinal bacteria," 2006, European Food Research and Technology, 222 pp. 737-740.
Brooks, A. W., et al., "Gut microbiota diversity across ethnicities in the United States," 2018, Plos Biology 16: e2006842.
Bucci, V., and Xavier, J., "Towards predictive models of the human gut microbiome," 2014, Journal of Molecular Biology, 426 pp. 3907-3916.
Camilleri, M., et al., "Clinical guideline: management of gastroparesis," 2013, American Journal of Gastroenterology, 108(1) pp. 18-37.
Caporaso, J. G., et al., "Ultra-high-throughput microbial community analysis on the Illumina HiSeq and MiSeq platforms," 2012, ISME Journal, 6 pp. 1621-1624.
Cho, I., and Blaser, M., "Applications of next-generation sequencing the human microbiome: at the interface of health and disease," 2012, Nature Reviews Genetics, 13 pp. 260-270.
Costello, E. K., et al., "Bacterial community variation in human body habitats across space and time," 2009, Science, 326 pp. 1694-1697.
Costello, E. K., et al., "The application of ecological theory toward an understanding of the human microbiome," 2012, Science, 336 pp. 1255-1262.
Cottingham, K. L., Lennon J. T., and Brown B. L., "Knowing when to draw the line: designing more informative ecological experiments," 2005, Frontiers in Ecology and the Environment, 3 pp. 145-152.
Cremer, J., Arnoldini, M., and Hwa, T., "Effect of water flow and chemical environment on microbiota growth and composition in the human colon," 2017, Proceedings of the National Academy of Sciences of the United States of America, 114 pp. 6438-6443.
Crump, B. C., "Microbial biogeography along an estuarine salinity gradient: combined influences of bacterial growth and residence time," 2004, Applied and Environmental Microbiology, 70 pp. 1494-1505.
D'Argenio, V., and Salvatore, F., "The role of the gut microbiome in the healthy adult status," 2015, Clinica Chimica Acta, 451 pp. 97-102.
David, L. A., et al., "Diet rapidly and reproducibly alters the human gut microbiome," 2014, Nature, 505 pp. 559-563.
Dietze, M. C., et al., "Iterative near-term ecological forecasting: Needs, opportunities, and challenges," 2018, Proceedings of the National Academy of Sciences of the United States of America, 115 pp. 1424-1432.
Donaldson, G. P., Lee S. M., and Mazmanian, S. K., "Gut biogeography of the bacterial microbiota," 2016, Nature Reviews Microbiology, 14 pp. 20-32.
Findley, K., et al., "Health Disparities and the Microbiome," 2016, Trends in Microbiology, 24 pp. 847-850.
Fischer, M., et al., "Assessment of small intestinal transit times in ulcerative colitis and Crohn's disease patients with different disease activity using video capsule endoscopy," 2017, AAPS PharmSciTech, 18 pp. 404-409.
Flynn, K., et al., "High throughput toxicology and disease modeling using MimEX GI, a Novel 3-D gastrointestinal tissue model," 2018.
Garud, N. R., et al., "Evolutionary dynamics of bacteria in the gut microbiome within and across hosts," 2017, bioRxiv Preprint doi: https://doi.org/10.1101/210955.
Goodrich, J. K., et al., "Human genetics shape the gut microbiome," 2014, Cell, 159 pp. 789-799.
Grimm, V., et al., "A standard protocol for describing individual-based and agent-based models," 2006, Ecological Modelling, 198 pp. 115-126.
Gross, B. C., "Evaluation of 3D printing and its potential impact on biotechnology and the chemical sciences," 2014, Analytical Chemistry, 86 pp. 3240-3253.
Lennon, J. T., and Martiny, J. B. H., "Rapid evolution buffers ecosystem impacts of viruses in a microbial food web," 2008, Ecology Letters, 11 pp. 1178-1188.
Gumennik, A., et al., "Confined in-fiber solidification and structural control of silicon and silicon-germanium microparticles," 2017, Proceedings of the National Academy of Sciences of the United States of America, 114 pp. 7240-7245.
Gumennik, A., et al., "Silicon-in-silica spheres via axial thermal gradient in-fibre capillary instabilities," 2017, Nature Communications, 4 pp. 2216.
Hellweger, F. L., et al., "Advancing microbial sciences by individual-based modelling," 2016, Nature Reviews Microbiology, 14 pp. 461-471.
Hidalgo, I. J., Raub, T. J., and Borchardt, R. T., "Characterization of the human-colon carcinoma cell-line (CACO-2) as a model sysem for intestinal epithelial permeability," 1989, Gastroenterology, 96 pp. 736-749.
Huttenhower, C., et al., "Structure, function and diversity of the healthy human microbiome," 2012, Human Microbiome Project, Nature, 486 pp. 207-214.
Jones, S. E., and Lennon, J. T., "A test of the subsidy-stability hypothesis: the effects of terrestrial carbon in aquatic ecosystems," 2015, Ecology, 96 pp. 1550-1560.
Kau, A. L., et al., "Human nutrition, the gut microbiome, and the immune system," 2011, Nature, 474 pp. 327-336.
Kawasaki, S., et al., "Response of the microaerophilic *Bifidobactetium* species, *B. boum* and *B. thermophilum*, to oxygen," 2006, Applied and Environmental Microbiology, 72 pp. 6854-6858.
Kelly, J. R., et al., "Breaking down the barriers: the gut microbiome, intestinal permeability and stress-related psychiatric disorders," 2015, Front Cell Neurosci, 9 pp. 392.
Kim, H. J., et al., "Contributions of microbiome and mechanical deformation to intestinal bacterial overgrowth and inflammation in a human gut-on-a-chip," 2016, Proceedings of the National Academy of Sciences of the United States of America, 113:E7-E15.
Koskella, B., Hall, L. J., and Metcalf, C. J. E., "The microbiome beyond the horizon of ecological and evolutionary theory," 2017, Nature Ecology & Evolution, 1 pp. 1606-1615.
Kozich, J. J., et al., "Development of a dual-index sequencing strategy and curation pipeline for analyzing amplicon sequence data on the MiSeq Illumina sequencing platform," 2013, Applied and Environmental Microbiology, 79(17) pp. 5112-5120.
Lande, R., and Arnold, S. J., "The measurement of selection on correlated characters," 1983, Evolution, 37 pp. 1210-1226.
Langmead, B., and Salzberg, S. L., "Fast gapped-read alignment with Bowtie 2," 2012, Nature Methods, 9(4) pp. 357-359.
Lattari, J., "Improving bioprocess control and optimization: in-line dissolved carbon dioxide measurement in bioproduction," 2017, Genetic Engineering & Biotechnology News, 38 pp. 24-25.
Lau, J. A., and Lennon, J. T., "Rapid responses of soil microorganisms improve plant fitness in novel environments," 2012, Proceedings of the National Academy of Sciences of the United States of America, 109 pp. 14058-14062.
Lee, S. M., et al., "Bacterial colonization factors control specificity and stability of the gut microbiota," 2013, Nature, 501 pp. 426-429.
Lennon, J. T., et al., "Mapping the niche space of soil microorganisms using taxonomy and traits," 2012, Ecology, 93 pp. 1867-1879.
Lennon, J. T., and Jones, S. E., "Microbial seed banks: the ecological and evolutionary implications of dormancy," 2011, Nature Reviews Microbiology, 9 pp. 119-130.
Lennon, J. T., and Lehmkuhl, B. K., "A trait-based approach to bacterial biofilms in soil," 2016, Environmental Microbiology, 18 pp. 2732-2742.
Chaussabel et al., "Assessing the human immune system through blood transcriptomics," 2010, BMC Biology, 8 pp. 1-14.
Colombe et al., "Single-mode optical fiber for high-power, low-loss UV transmission," 2014, Optics Express, 22(16) pp. 19783.

(56) References Cited

OTHER PUBLICATIONS

Faccini de Lima et al., "Towards Digital Manufacturing of Smart Multimaterial Fibers," 2019, Nanoscale Research Letters, 14(209) pp. 1-16.
Farajikhah et al., "Thermally drawn biodegradable fibers with tailored topography for biomedical applications," 2020, Journal of Biomedical Materials Research Part B Applied Biomaterials, 109(5) pp. 733-743.
Gumennik, A. and Sen, C., "Hierarchically vascularized organoids by fiber-embedding bioprinting," 2020, Wellcome Leap Solicitation for Human Organs, Physiology, and Engineering.
Lee, J. et al., "Conductive fiber-based ultrasensitive textile pressure sensor for wearable electronics," 2015, Advanced Materials, 27(15) pp. 2433-2439.
Maleki et al., Whispering gallery mode lithium niobate microresonators for photonics applications, 2003, Proceedings of SPIE, 5104.
Monro et al., "Sensing with Suspended-Core Optical Fibers," 2010, Opt. Fiber Technology, 16(6):343-356.
Powers et al., "Propagation of a topological transition: the Rayleigh instability", 1998, Phys Fluids 10(5):1052-1057.
Kotz et al. "Next generation 3D printing of glass: The emergence of enabling materials," Proc. SPIE 10804, Advanced Manufacturing Technologies for Micro- and Nanosystems in Security and Defence, 108040I (Oct. 8, 2018); doi: 10.1117/12.2323095.
Schaaf et al., "Defining the role of the tumor vasculature in antitumor immunity and immunotherapy," 2018, Cell Death and Disease, 9(2).
Shadman et al., "Microstructured Biodegradable Fibers for Advanced Control Delivery," 2020, Advanced Functional Materials, 30(13) pp. 1-9.
Song et al., "Vascular Tissue Engineering: Progress, Challenges, and Clinical Promise," 2018, Cell Stem Cell, 22(3) pp. 340-354.
Van der Elst et al., "3D Printing in Fiber-Device Technology," 2021, Advanced Fiber Materials.
Meira et al., "Degradation and viscoelastic properties of PLA-PCL, PGA-PCL, PDO and PGA fibres," 2010, Materials Science Forum, 636-637 pp. 825-832.
Wei et al., "Optoelectronic Fibers via Selective Amplification Of In-Fiber Capillary Instabilities," 2017, Advanced Materials, 29(1).
Williams et al., "Etch rates for micromachining processing—Part II," 2003, Journal of Microelectromechanical Systems, 12(6) pp. 761-778.
Zhong et "Nanophotonic rare-earth quantum memory with optically controlled retrieval," 2017, Science, 357 pp. 1392-1395.
Lennon, J. T., et al., "How, when, and where relic DNA biases estimates of microbial diversity," 2018, Mbio 9: e00637-00618.
Leone, A., et al., "Development of a prototype malaxer to investigate the influence of oxygen on extra-virgin olive oil quality and yield, to define a new design of machine," 2014, Biosystems Engineering, 118 pp. 95-104.
Levy, S. F., et al., "Quantitative evolutionary dynamics using high-resolution lineage tracking," 2015, Nature, 519 pp. 181-186.
Ley, R. E., Peterson, D. A., and Gordon, J. I., "Ecological and evolutionary forces shaping microbial diversity in the human intestine," 2006, Cell, 124 pp. 837-848.
Lloyd-Price, J., Abu-Ali, G., and Huttenhower, C., "The healthy human microbiome," 2016, Genome Medicine, 8.
Locey, K. J., Fisk, M. C., and Lennon, J. T., "Microscale insight into microbial seed banks," 2017, Frontiers in Microbiology, 7(2040).
Locey, K. J., and Lennon, J. T., "A modeling platform for the simultaneous emergence of ecological patterns," 2017, PeerJ Preprints, 5:e1469v1463.
Locey, K. J., and Lennon, J. T., "A residence time framework for biodiversity," 2018, PeerJ Preprints, 5:e2727v2722.
Love, M. I., Huber, W., and Anders, S., "Moderated estimation of fold change and dispersion for RNA-seq data with DESeq2," 2014, Genome Biology, 15.
Lundberg, D. S., et al., "Defining the core *Arabidopsis thaliana* root microbiome," 2012, Nature, 488 pp. 86-90.

Macfarlane, S., and Dillon, J. F., "Microbial biofilms in the human gastrointestinal tract," 2007, Journal of Applied Microbiology, 102 pp. 1187-1196.
Magnusson, K. R., et al., "Realtionships between diet-related changes in the gut microbiome and cognitive flexibility," 2015, Neuroscience, 300 pp. 128-140.
Martiny, J. B. H., et al., "Microbiomes in light of traits: A phylogenetic perspective," 2015, Science, 350(6261) pp. aac9323.
Mathys, S., et al., "PCR and real-time PCR primers developed for detection and identification of Bifidobacterium thermophilum in faeces," 2008, BMC Microbiology, 8 pp. 179.
Minekus, M., "Models of the gastrointestinal tract to study microbial interactions," 2005, Microbial Ecology in Growing Animals, 2 pp. 142-154.
Moldovan, N. I., Hibino, N., and Nakayama, K., "Principles of the Kenzan method for robotic cell spheroid-based three-dimensional bioprinting," 2017, Tissue Engineering Part B—Reviews, 23 pp. 237-244.
Molly, K., Woestyne, M. V., and Verstraete, W., "Development of a 5-step multichamber reactor as a simulation of the human intestinal microbial ecosystem," 1993, Applied Microbiology and Biotechnology, 39 pp. 254-258.
Monod, J., "La technique de culture continue Théorie et applic," 1950, Ann Inst Pasteur, 79 pp. 390-410.
Muller-Lissner, S. A., et al., "Myths and misconceptions about chronic constipation," 2005, American Journal of Gastroenterology, 100 pp. 232-242.
Murphy, S. V., and Atala, A., "3D bioprinting of tissues and organs," 2014, Nature Biotechnology, 32 pp. 773-785.
Murray J. A., et al., "No difference between latiglutenase and placebo in reducing villous atrophy or improving symptoms in patients with symptomatic celiac disease," 2017, Gastroenterology, 152 pp. 787-798.
Niba, E. T. E., et al., "A genome-wide approach to identify the genes involved in biofilm formation in *E. coli.*," 2007, DNA Research, 14 pp. 237-246.
Novick, A., and Szilard, L., "Experiments with the chemostat on spontaneous mutations," 1950, Proceedings of the National Academy of Sciences of the United States of America, 36 pp. 708-719.
Owczarek, D., et al., "Diet and nutritional factors in inflammatory bowel diseases," 2016, World Journal of Gastroenterology, 22 pp. 895-905.
Pedron, T., et al., "A crypt-specific core microbiota resides in the mouse colon," 2012, mBio 3: e00116-12.
Pepper, J. W., and Rosenfeld, S., "The emerging medical ecology of the human gut microbiome," 2012, Trends in Ecology & Evolution, 27 pp. 381-384.
Pirt, S. J., "The maintenance energy of bacteria in growing cultures," 1965, Proceedings of the Royal Society London B Biological Sciences, 12 pp. 224-231.
Reese, A. T., and Dunn, R. R., "Drivers of microbiome biodiversity: a review of general rules, feces, and ignorance," 2018, mBio, 9(4) e01294-18.
Rossi, M., et al., "Fermentation of fructooligosaccharides and inulin by bifidobacteria: a comparative study of pure and fecal cultures," 2005, Applied and Environmental Microbiology, 71 pp. 6150-6158.
Roy, S. K., Akramuzzaman, S. M., and Akbar, M. S., "Persistent diarrhea: total gut transit time and its relationship with nutrient absorption and clinical response," 1991, Journal of Pediatric Gastroenterology and Nutrition, 13 pp. 409-414.
Sender, R., Fuchs, S., and Milo, R., "Revised estimates for the number of human and bacteria cells in the body," 2016, Plos Biology, pp. 1-14.
Shah, P., et al.,"A microfluidics-based in vitro model of the gastrointestinal human-microbe interface," 2016, Nature Communications, 7 pp. 11535.
Shreiner, A. B., Kao, J. Y., and Young, V. B., "The gut microbiome in health and in disease," 2015, Current Opinion in Gastroenterology, 31 pp. 69-75.
Slavin, J., "Fiber and prebiotics: Mechanisms and health benefits," 2013, Nutrients, 5 pp. 1417-1435.

(56) References Cited

OTHER PUBLICATIONS

Smith, D. C., and Azam, F., "A simple, economical method for measuring bacterial protein synthesis rates in seawater using 3H-leucine," 1992, Marine Microbial Food Webs, 6 pp. 107-114.

Smith, H. L., and Waltman, P., "The Theory of the Chemostat: Dynamics of Microbial Competition," 1995, Cambridge University Press, New York.

Tanner, S. A., et al., "Bifidobacterium thermophilum RBL67 impacts on growth and virulence gene expression of *Salmonella enterica* subsp *enterica* serovar Typhimurium," 2017, BMC Microbiology, 16 pp. 46.

Tropini, C., et al., "The gut microbiome: connecting spatial organization to function," 2017, Cell Host & Microbe, 21 pp. 433-442.

Turnbaugh, P. J., et al., "A core gut microbiome in obese and lean twins," 2009, Nature, 457 pp. 480-487.

Verhoeckx, K., et al., editors. "The Impact of Food Bioactives on Health: in vitro and ex vivo models," 2015, Cham (CH): Springer.

Verdu, E. F., Galipeau, H. J., and Jabri, B., "Novel players in coeliac disease pathogenesis: role of the gut microbiota," 2015, Nature Reviews Gastroenterology & Hepatology, 12 pp. 497-506.

Waldron, D., "In transit," 2015, Nature Reviews Microbiology, 13 pp. 659-659.

Walter, J., and Ley, R. E., "The human gut microbiome: ecology and recent evolutionary changes," 2011, Annual Review of Microbiology, 65 pp. 411-429.

Xiao, L., et al., "A catalog of the mouse gut metagenome," 2015, Nature Biotechnology, 33 pp. 1103-1108.

Xu, Z., and Knight, R., "Dietary effects on human gut microbiome diversity," 2015, British Journal of Nutrition, 113:S1-S5.

Zhao, S., et al., "Adaptive evolution within the gut microbiome of individual people," 2017, bioRxiv Preprint doi: https://doi.org/10.1101/208009.

Zhu, C. Z., et al., "Electrochemical sensors and biosensors based on nanomaterials and nanostructures," 2015, Analytical Chemistry, 87 pp. 230-249.

\* cited by examiner

GUT BIOREACTOR AND METHODS FOR MAKING THE SAME

CROSS-REFERENCE TO RELATED APPLICATIONS

This application claims priority to U.S. Provisional Application Serial No. 63/014,430, filed on Apr. 23, 2020, the contents of which are incorporated herein by reference.

Cross-reference is made to U.S. application Ser. No. 17/239,322, filed Apr. 23, 2021, titled "METHODS FOR CREATING THREE DIMENSIONAL BIOSYNTHETIC TISSUE," now U.S. Patent Application Publication No. 2021/0330864. Cross-reference is made to U.S. Application Ser. No. 17/239,100, filed Apr. 23, 2021, titled "VERY LARGE SCALE INTEGRATION FOR FIBERS (VL SI-Fi)," now U.S. Patent Application Publication No. 2021/0333131. The contents of each of these applications are incorporated herein by reference in their entireties. Neither of these cross-referenced applications is admitted to be prior art with respect to present application by its mention in the cross-reference section.

BACKGROUND

Over the past decade, advances in molecular biology and bioinformatics have revealed that plants and animals across the tree of life engage in symbiotic relationships with hyper-diverse microbiomes (Costello et al. 2009, Lundberg et al. 2012, and Xiao et al. 2015). In fact, humans are colonized by trillions of bacteria that collectively make up a microbiome. Diet, genetics, ethnicity, and immune status contribute to the abundance, diversity, and activity of host microbiomes (Findley et al. 2016, Lloyd-Price et al. 2016, and Brooks et al. 2018). However, even among closely related individuals with similar lifestyles, microbiome composition can be quite distinct (Turnbaugh et al. 2009, Goodrich et al. 2014).

Many of these microorganisms have a beneficial effect on host fitness. More than 1,000 species of bacteria reside in the colon where they aid in digestion, reduce "leaky gut", and synthesize essential vitamins while regulating the production of hormones and neurotransmitters. However, microbiomes are also implicated in a wide range of disorders and diseases (Cho and Blaser 2012, Shreiner et al. 2015) that negatively influence host health and fitness. Gut microbiomes have also been implicated in the rise of non-communicable diseases, e.g. irritable bowel syndrome. Owing to societal shifts in nutrition and overuse of antibiotics, altered microbiomes may contribute to the prevalence of allergies, asthma, inflammation, diabetes, and anxiety. Observational studies often report correlations between gut microbiome composition and the behavior, diet, and age of hosts. Such findings raise questions about whether there are general rules, theories, or frameworks that can help predict and manage the structure, function, and stability of gut microbiomes (Pepper and Rosenfeld 2012, Bucci and Xavier 2014, Reese and Dunn 2018).

The mechanisms underlying microbiome effects on host performance and fitness remain unclear and deciphering interactions and emergent phenomena is one of the greatest challenges facing microbiome science. A common approach is to interpret fecal samples as integrators of gut complexity and rely on epidemiological inference to gain insight into relationships between microbiomes and their host (e.g., Huttenhower et al. 2012). More mechanistic insight can be gained from in vivo models (e.g., mouse) where it is easier to control for host attributes (diet, genetics, environment), but organismal constraints and individual-level variation still interferes with a first-principles understanding of gut microbiome functioning. To address these shortcomings and complement "top down" approaches, a number of in vitro models have been used to tease apart eco-evolutionary interactions among microbes in gut-like habitats (Minekus 2005). For example, the simulated human intestinal microbial ecosystem (SHIME) consists of a five-step multi-chamber reactor (Molly et al. 1993). While it allows for different microbial inocula and embraces fluctuations in environmental conditions (Van de Wiele et al. 2015), SHIME lacks microscale features that are typical of mammalian guts (Donaldson et al. 2016) and its large size (>5 L) limits replication and experimental design. An entirely different in vitro approach is centered around "gut on a chip" technology where human epithelial cells are coated onto porous flexible membranes (Bein et al. 2018). Nanoliter to microliter operating volumes ensure laminar flow making the chip-models desirable for drug development (Hidalgo et al. 1989), but they have also revealed connections between mechanical deformation and bacterial overgrowth (Kim et al. 2016), a problem that arises in ileus patients where peristalsis is disrupted. While the chip technology represents a major bioengineering feat, current models only support a small number of bacterial species (<10) for a few days (Kim et al. 2016, Shah et al. 2016), suggesting that gut-on-a-chip models may not be best suited for tackling ecological and evolutionary questions about microbial communities at the whole-organ scale. As such, carefully controlled and properly replicated experimental studies testing theoretically grounded predictions are needed to establish a foundation that links microbiome dynamics to the nutrition and physical features of the mammalian gut.

In light of the above, a systems-level approach that focuses on fundamental ecological and evolutionary processes that influence the structure of multispecies microbial communities is desirable. In particular, integrated physical and computational models with living tissue and microscale biosensing and biofunctionalization that facilitates better information on interactions at the cellular level, while decreasing the drawbacks of microfluidics or animal studies is required.

SUMMARY

In one aspect, the disclosure provides a bioreactor comprising a cylindrical body formed to include a reactor region therein, a first member, and a second member. In some aspects, the first member extends into the reactor region a first distance. In some embodiments, the first member is formed to include a plurality of protuberances that extend from a surface of the first member into the reactor region.

In some embodiments, the second member located spaced apart from the first member and extends into the reactor region a second distance. In some embodiments, the second distance is generally less than the first distance of the first member. In some embodiments, the second member is formed to include a plurality of protuberances that extend from a surface of the second member into the reactor region.

In some embodiments, the first member and the second member cooperate to form a crypt region located between a portion of the protuberances from the first member and a portion of the protuberances of the second member.

In another aspect, the disclosure provides a method for forming a gut bioreactor.

BRIEF DESCRIPTION OF THE DRAWINGS

FIG. 5A shows fibers are fed through the print head nozzle with bioink as the base for the 3-D construct of the reactor. FIG. 5B shows flow of microorganisms (Q) through the gut volume (V) with embedded fibers in the encoded villi (Φ). FIG. 5C shows biofunctional and biosensing fibers are drawn at high temperature from a rod composed of a variety of functional materials. During draw process, the cross-sectional area of the rod or preform will be preserved, allowing for radial arrangement control of the fiber. Using a post-processing method initiating capillary instability in the core of the fiber by controlled heat, the axial direction can be manipulated to transformed linear cores into periodic spheres;

DETAILED DESCRIPTION

Figure 1:
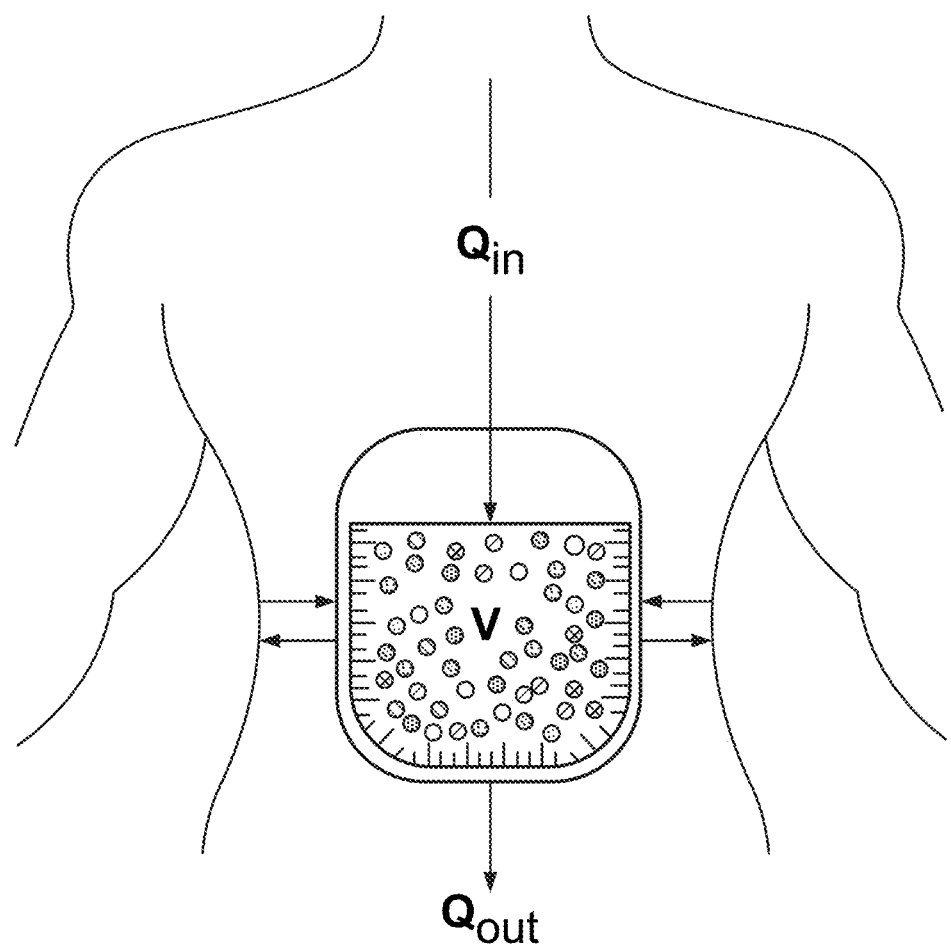
FIG. 1 illustrates the complexities associated with the gut microbiome.
Figure 2:
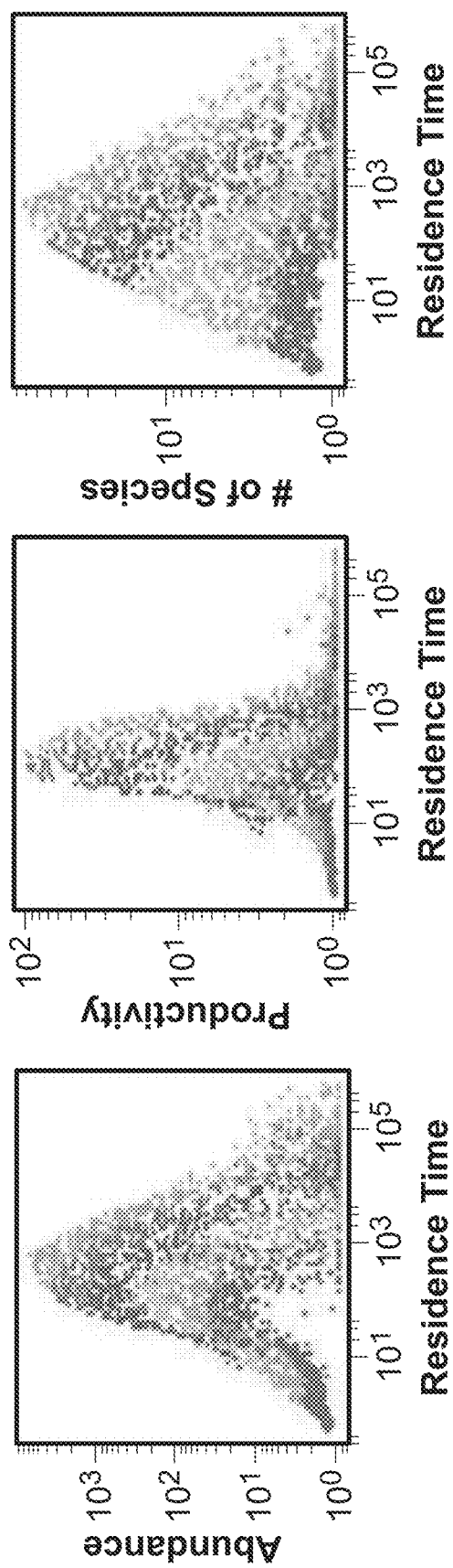
FIG. 2 shows how residence time (volume/flow rate) influences microbial communities.
Figure 3A:
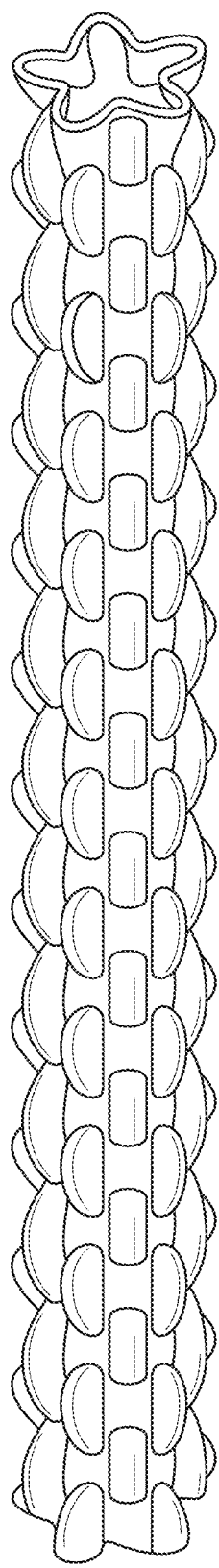
FIGS. 3A-C show 3D models of gut sections FIG. 3A and FIG. 3B using computer-aided design (CAD) and FIG. 3C shows a prototype of a 3-D printed model.
Figure 3B:
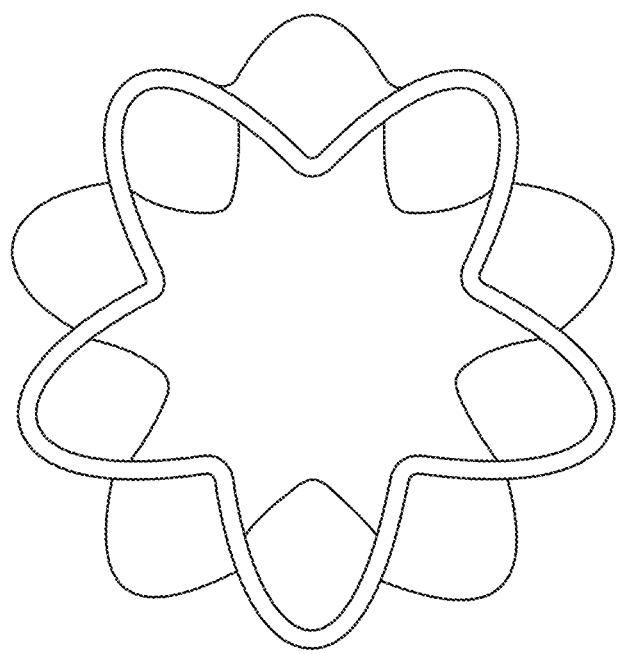
Figure 3C:
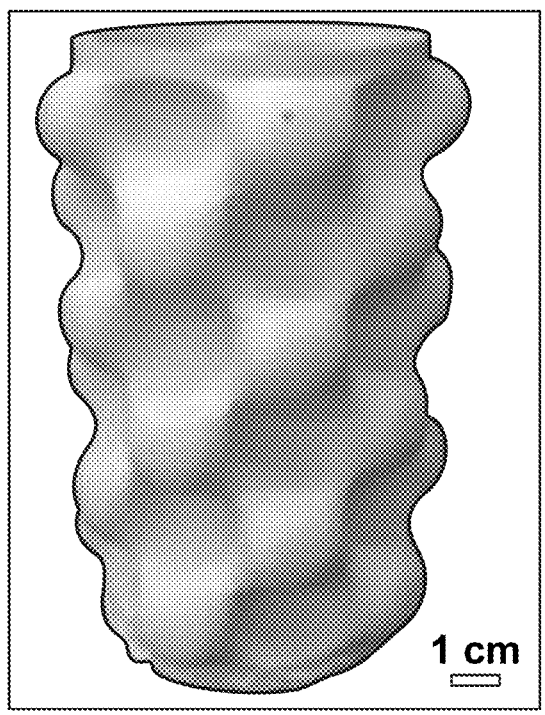

The current disclosure outlines models of the gut microbiome. The present disclosure generates insight into physical and nutritional factors that underlie gastrointestinal and cognitive disorders, which can be triggered by stressors such as diet intake, under nutrition, and environmental extremes.

The present disclosure provides a methodology for creating biosynthetic tissue, for example a gut model. This methodology allows the elucidation of critical elements of gut complexity using a combination including theory, 3D-printed bioreactors, and experimental evolution. The modeling framework described herein provides a platform for exploring the physical complexity of flowing environments and the diversity of microbial systems. The following discussion sets forth a framework for incorporating complex features of the mammalian gut, test predictions of in vitro models.

In particular, the disclosure is directed to a platform of 3D-printed gut bioreactors with sensing capabilities to test theoretical predictions about trade-offs among functional traits in relation to gut features (e.g., villi and folds), which are important for the assembly and structure of gut microbiomes.

Specifically, in one embodiment the present disclosure provides tissue engineering approach where cell-containing material is intimately meshed with fiber-construct scaffold (whether in the form of needles array, or supplied as part of bioink feedstock, or fabricated first and then infiltrated with cells, as in classical biomimetic scaffolds). The fiber scaffold has active capabilities (micromechanical, microfluidic, microelectronic) that mimic biofunctional or biosensing modalities, such as musculature, vasculature, and innervation. In addition, the tissue engineering approach described herein helps address a bottleneck of supplying bioprinted tissue with realistic microstructure. Possible applications are drug toxicity tests (printed liver tissue) and examination of intestine functioning on the microbiotic level.

In another embodiment a methodology for investigating the of complexity of microbiome is provided, where the investigation of biofilm formation, heterogeneous interactions between various players in the variety of microorganisms, nutrition processes, inflammation conditions, biochemistry of digestion are all examined in synthetic or biosynthetic gut models embedding sensors that allow monitoring the microbiological processes with high spatiotemporal resolution. For example, the present disclosure describes using gut bioreactors for investigation of microbiome, with fiber-device-embedding biosynthetic tissue engineering being an example of the implementation of the approach discussed herein.

In another specific embodiment, the present disclosure provides an experimental platform to test theoretical predictions about trade-offs among functional traits in relation to the size distributions of villi, which are important for the assembly and structure of gut microbiomes. As discussed below the present disclosure provides a platform for the assessment of biochemistry in cellular and bacteria community interactions. One aspect of the disclosure is that the platform described herein can be applied to observing microbiological activity in response to an artificial environment. Experimental results are simulated and the computational model conclusions provide information to feed back into the experimental work. This loop of theoretical and practical research will provide, with a number of iterations and time, desirable circumstances for providing information concerning the environment being tested, at both the microscale and the macroscale.

The current disclosure elucidates critical elements of gut complexity using 3D-printed bioreactors. It is based on a modeling framework that explores the physical complexity of flowing environments and the diversity of microbial systems. The current disclosure expands on that framework to incorporate complex features of the mammalian gut and tests its predictions with in vitro models.

One particular aspect of the disclosure is a dynamic artificial gut model integrating both experiments. The gut model includes a bacterial bioreactor with biosensing and biofunctionalized features that provides a realistic macroscale and microscale test of microenvironment communities.

One approach for deciphering interactions and emergent phenomena is to interpret fecal samples as integrators of gut complexity and rely on epidemiological inference to gain insight into relationships between microbiomes and their host. Enhanced insight of these phenomena can be gained from in vivo models (e.g., mouse) which lend themselves to controlling host attributes (diet, genetics, and environment). However, organismal constraints and individual-level variation tend to interfere with the understanding of gut microbiome functioning. These shortcomings can be addressed by using in vitro models to assess eco-evolutionary interactions among microbes in gut-like habitats. An example of an in vitro, utilizes a simulated human intestinal microbial ecosystem (SHIME) which consists of a five-step multi-chamber reactor (Molly et al. 1993). While this model allows for different microbial inocula and embraces fluctuations in environmental conditions (Van de Wiele et al. 2015), it lacks microscale features that are typical of mammalian guts (Donaldson et al. 2016) and its large size (>5 L) limits replication and experimental design. The in vitro "gut on a chip" technology allows nanoliter to microliter operating volumes to ensure laminar flow. These "gut on a chip" models are desirable for drug development, and they have revealed connections between mechanical deformation and bacterial overgrowth a problem that arises in ileus patients where peristalsis is disrupted. However, a drawback of the chip technologies is that they only support a small number of bacterial species (<10) for a few days. As such, these technologies are not well suited for tackling ecological and evolutionary questions about microbial communities at the whole-organ scale.

Accordingly, 3D bioreactors that scale important anatomical features of the mammalian gut are desired. Compared to existing in vitro models, 3D bioreactors can show more realistic fluidic dynamics, which is important for addressing how residence time, villi, and resources interact in systems with multiphase flow. These reactors can be printed with a range of materials, including epithelial cells, which will be embedded with nanofibers that are capable of biosensing and biostimulation. Through the combination of expanded simulations and experimental tests, a better understanding and prediction of microbiome dynamics can be achieved with implications for host nutrition and health.

In accordance with one embodiment, a bioengineering system according to the present disclosure may be applied to artificial gut models. For example, such a bioengineering system may be used to study microbiome complexity in nutrition-related processes. Fibers embedded into a printed gut bioreactor may ultrasonically map buildup of microflora biofilm on the gut walls and may enable monitoring of changes in $CO_2$, pH, and $O_2$ accompanying this process. In such an example, bioinks for the artificial gut models will incorporate intestinal epithelial cells typical in real guts.

In some embodiments, electrochemistry offers a wide variety of methods to stimulate and sense cellular and bacterial environments. In some embodiments, a library of fibers has been proposed to help monitor the experiment in terms of the bacterial and cellular growth and interactions within. For example, part of the experiment may observe standard indicators such as pH, growth of bacterial population density by observing optical density before and after trials using a spectrophotometer. In addition to standard laboratory observations, multi-material fiber technology (VLSI-Fi) can help add controlled biostimulation and biosensing to the model. These experimental conditions can be modelled and simulated in parallel to create a feedback loop between the experiment and theory. In some embodiments, biosensing may include: 1) sensing stress and motion in selective areas of the gut and understanding inner fluid dynamics may be useful to understand how the mass peristaltic flow affects the gut biofilm and epithelium; 2) observing changes in density may signal growth in certain areas of the gut, and may be observed using ultrasound imaging (also known as sonography), which correlates to the presence of internal structure within the gut model; and 3) microfluidics in sampling some fluid volume at specific locations within the bioreactor for analysis of microbial colonies at different stages of residency in terms of time and position along the gut. In some embodiments, the introduction of biostimulation and biosensing capabilities may be done by interweaving fiber devices in the wall of the gut model. In one aspect, the material in the bioreactor is viscous which helps to introduce fiber devices. In some alternative embodiments that employ a more rigid structure, cavities can be inserted to introduce the fiber into a bioreactor. In one embodiment, an optical fiber may be introduced into the bioreactor.

When developing a biologically relevant gut model, it is important to ensure that key elements of the GI tract are recapitulated. Ideally, the model should be able to maintain a microbial community in an anaerobic environment with a stable pH. Also, these conditions should be physiologically similar to the ileum, the human GI tract segment that our gut model most closely resembles.

In the gut bioreactors, oxygen levels from the gut media before entering the model were significantly higher than the oxygen levels of the spent media exiting the model (FIG. 1., t=4.1015, p=0.025). The oxygen level of the spent media is very near 0 mg/L, showing that while an anaerobic environment is not imposed on the gut model, it develops within the first 24 hours of an experimental run and is maintained throughout a week run. The split oxygen levels in the feed are due to decreases in oxygen level seen over the 24-hour period each feed tank is attached to the system. In addition to an anaerobic environment, a pH of 7 is maintained which is like that of the human ileum (Walter & Ley, 2011).

In preliminary trials of complex fecal microbial community inoculum with daily immigration, the bacterial community reached equilibrium densities of $\sim 10^9$ cells/mL ($10^{8.96}$+/$-10^{0.12}$) with a low coefficient of variation (CV=11.7%) in the bioreactors meaning these populations are quite stable and physiologically similar to the distal small intestine in vivo (Walter & Ley, 2011). In this preliminary experiment, we observed a potential secondary stable state of microbial abundance that occurred after day 14.

In some embodiments, the gut bioreactor is capable of culturing bacterial cells for at least one day, at least two days, at least three days, at least four days, at least five days, at least six days, at least seven days, at least eight days, at least nine days, at least ten days, at least eleven days, at least twelve days, at least thirteen days, or at least fourteen days.

The platform of the present disclosure can be utilized to address questions pertaining to the ecology and evolution of microbial communities using an approach where 3D spatially explicit modeling and experimentation are uniquely aligned. Relying on iterative feedback between computational models and experiments, theoretical predictions can be generated, tested, and refined.

First digital models using computer aided design (CAD) software that are scale-accurate instructions for the precise design of functional materials are created. The bioreactors can be manufactured using stereo lithography (SLA), a laser based technique that allows for precise and smooth printed high-resolution 3D constructs of small volumes at fast build times (Gross et al. 2014, Gumennik and Eltony 2017).

Moreover, printing reactors with a Form 2 printer using Dental SG resin a style of resin used readily in dental settings, which is an autoclavable and biocompatible photopolymer, printed on the SLA Form 2 printer where each layer of resin is cured to the previous layer can be utilized to prepare to construct 3D-printed bioreactors.

Figure 4:
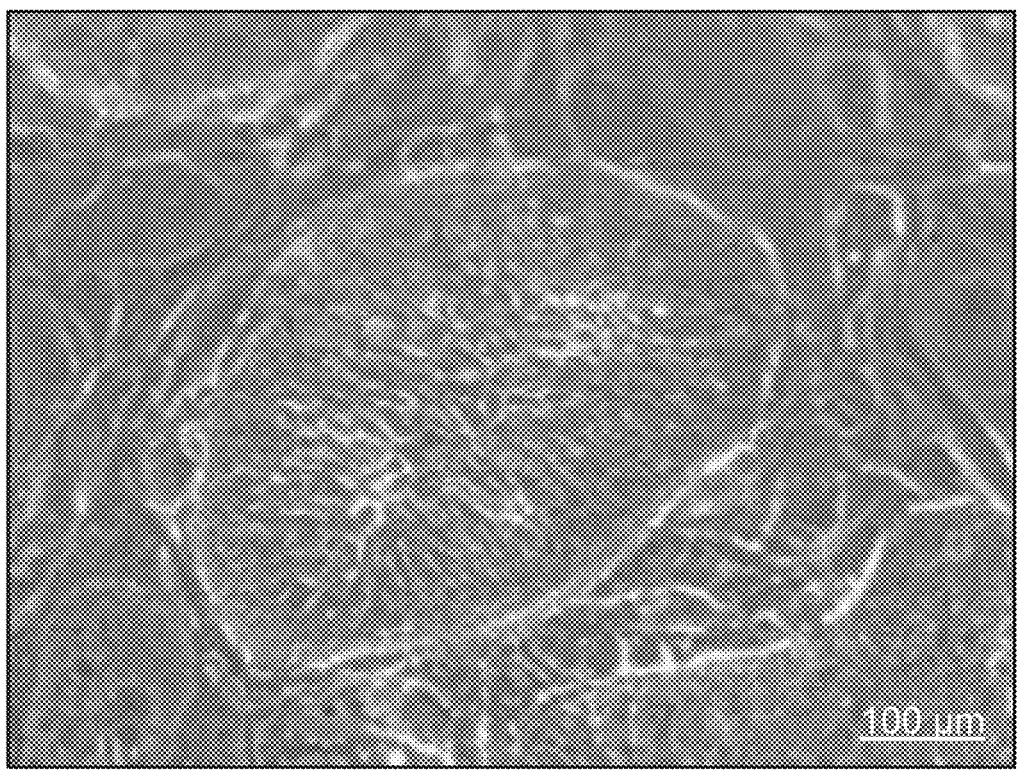
FIG. 4 shows colon epithelial cells grown on top of a feeder fibroblast layer in the MimEX system (from Biotechne) and the formation of microvilli-like features.

However, a more desirable bioreactor can be created utilizing bioprinting. One advantage of bioprinting is that it enables fabrication of parts and devices that take on the characteristics of tissues and organs. As opposed to the above-discussed methods of creating bioreactors, which use biologically inert materials, 3D bioprinting uses living cells as bioink. (Faccini de Lima et al. Nanoscale Research Letters (2019) 14:209). Bioprinting is particularly advantageous because it can be used in translational medicine for wound healing, repair of vascular networks, and bone reconstruction. One approach for bioprinting is a 'scaffold-free' (cells-only) method (Moldovan et al. 2017), which can be implemented using a Regenova bioprinter. This bioprinter places cell spheroids, e.g. intestinal smooth muscle cells and intestinal epithelial cells, on a microneedle array. The individual spheroids then fuse together and create the undulating geometry of the gut with folds that simulate intestinal crypts, another feature that contributes to gut complexity (Pedron et al. 2012). Stem cells derived from the colon emerge on 'feeder' fibroblast layers in as little as one week and display microvilli-like structures, which are thought to be important for the assembly and structure of gut microbiomes (See FIG. 4 which shows colon epithelial cells grown on top of a feeder fibroblast layer in the MimEX system (from Bio-techne) and the formation of microvilli-like features).

Another approach for bioprinting is bioink-based printing where cells are incorporated into matrix-like gels such as alginate. Bioinks can be printed in a layer-by-layer fashion similar to FDM 3D printing and cells grow in the bioink printed structure. GelMA is a biocompatible hydrogel derived from gelatin to which methacrylate and methacrylamide groups are added. GelMA as a bioink provides an excellent extracellular matrix (ECM) to the cells to create tissue-like structures.

In some embodiments, commercially available human intestinal epithelium and enteroid kits may be used to culture into thin sheets and layered onto the wall of a 3D printed gut model. Various bioprinting technologies such as bioinkjet and bioplotters have shown an ability to print approximately realistic tissue compiling various cell types and layers. Layering of cell spheroids has been done by simple side-by-side automated deposition, by fluid delivery where spheroids are suspended in a nutritious viscous liquid, or by transfixing spheroids onto needles arranged in an array (also known as the Kanzan technique). In some embodiments, the printed cells are given a maturation period to let the cells grow and form a consolidated tissue structure. In the human body, cells are supported by the extracellular matrix (ECM), an essential group of proteins that provide structure and other functions to the tissue. In some embodiments, the bioink comprises substrates that are composed of a variety of organic or synthetic materials. In some embodiments, the bioink is provided in the form of solvents, hydrogels, polymers, aerogels, or foam scaffolds. In some embodiments, the bioink composition may be made of biocompatible materials that are often degradable. In some embodiments, once a layer is printed, it can be deposited onto the inner wall of the artificial gut model. In some embodiments, the inner wall comprises pores, and this porosity of the 3D printed wall offers a welcoming substrate for the cellular matrix to bind to and grow further. With the added flow of bacterial colonies through the gut model during an experiment, a user is able to observe interactions between the cells and the biofilm.

Figure 5A:
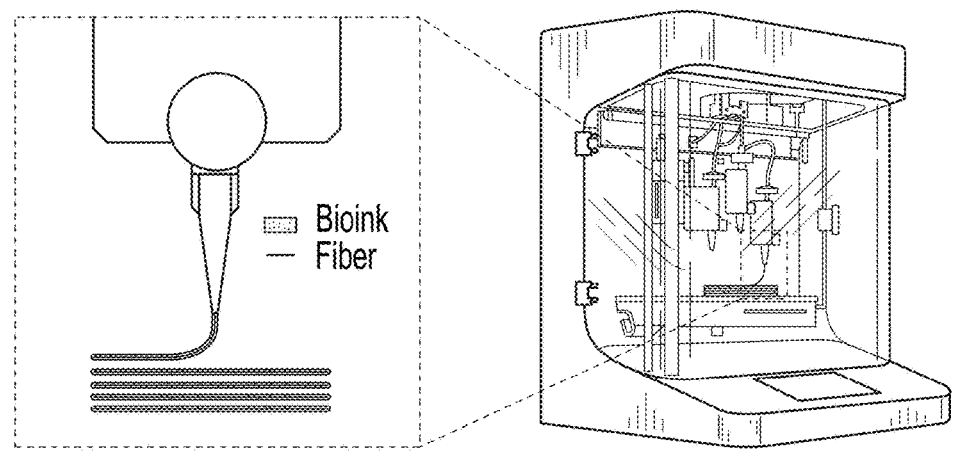
FIGS. 5A-C represents an overview of fiber technology in gut bioreactors.
Figure 5B:
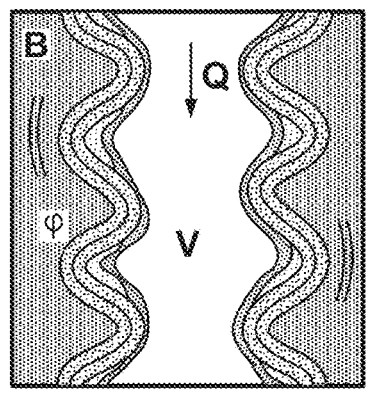
Figure 5C:
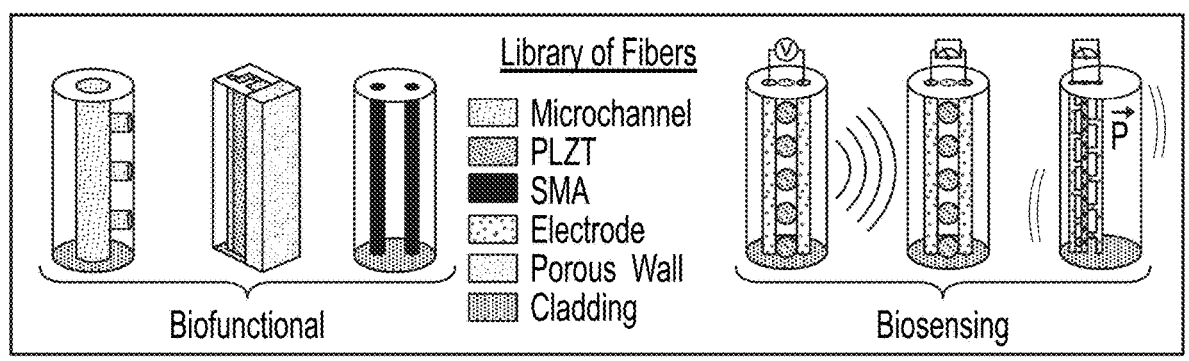
Figure 6A:
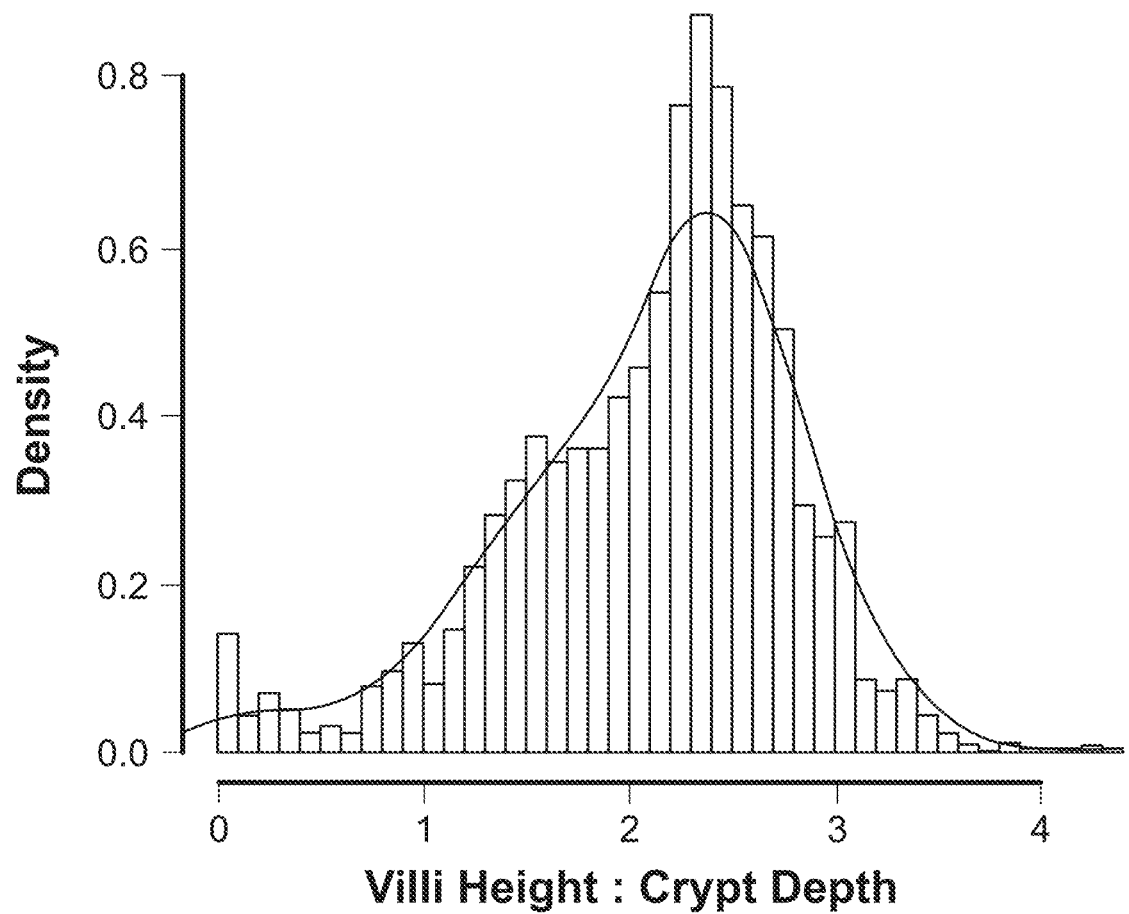
FIG. 6A shows, a size distribution of villi: crypt depth for small intestine biopsies in 1,345 celiac patients.
Figure 6B:
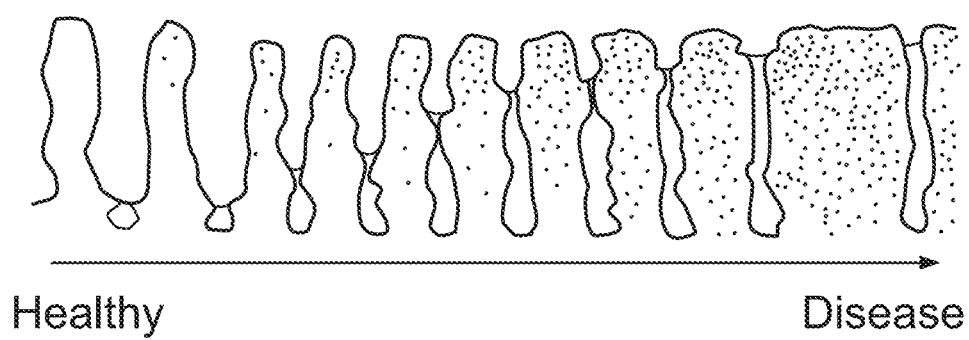
FIG. 6B shows that Villi: crypt ratios reflect loss of microscale complexity due to disease severity (reproduced from Murray et al. (2017))

Micro- and nano-fiber technology can be integrated into 3D-bioprinted reactors as illustrated in FIGS. 5A-C. Fiber technology can bring to conventional bioprinting and tissue engineering a new array of biological functionalities such as artificial vasculature, innervation and muscular motion. A microfluidic hollow fiber with periodic channels along its axis feeds epithelial cells or vascular epithelial growth factors to a desired location to support the natural growth of microvasculature. Piezoelectric elements measure surrounding cell density by ultrasound to provide a feedback of the microenvironments' conditions. This resembles the nervous system. Shape memory alloy wires provide peristaltic motion.

In some embodiments, the fiber senses the presence of a growth factor. In some embodiments, the growth factor may include epidermal growth factors (EGF), fibroblast growth factors (FGF), hepatocyte growth factors (HGF), transforming growth factors beta (TGF-β), and insulin-like growth factors (IGF).

In some embodiments, the presence of EGF may be a signal of cell growth and maturation. EGF stimulates cell growth, differentiation, and survival by binding its cognate receptor, found in urine, saliva, milk, tears, blood plasma, submandibular glands, and the parotid gland. It is regulated by iodine, which also plays a role in the maintenance of gastric tissue.

In some embodiments, the presence of FGF may be a signal of broad biological activities extracellularly and intracellularly including the stimulation of embryonic development, cell growth, morphogenesis, tissue repair, tumor growth and invasion, endothelial cell migration and proliferation, and angiogenesis. It is found in the extracellular matrix.

In some embodiments, the presence of HGF is a paracrine intracellular protein that stimulates cell growth, motility, and morphogenesis in embryonic organ myogenesis, adult organ regeneration, and wound healing. It is typically excreted by mesenchymal calls to monitor epithelial and endothelial cell behavior. It can also plays an influential role on haemopoietic progenitor cells and T cells.

In some embodiments, the presence of TGF-β is a cytokine stimulating other regulatory proteins, differentiation, chemotaxis, proliferation, and activation of immune cells by inducing target gene transcription. It is produced by all white blood cells and many other cell types. Due to its nature in regulating and differentiating stem cells, it is highly researched and used in infectious, autoimmune, and cancer disease therapy.

In some embodiments, the presence of IGF or somatomedin stimulates growth and controls blood glucose levels.

In some embodiments, the growth factors are introduced by nanofluidic methods using a hollow fiber with a porous membrane and a piezoelectric control for the delivery of very small volumes into the gut bioreactor.

In some embodiments, biosensing of growth factors is possible through biochemical substrates, but in our application of the gut model, we intend to observe how the growth factors affect the biological environment, for example through the observation of fluorescent markers in proteins that may represent how certain cell populations have grown or proliferated based on the insertion of one or more growth factors.

In some embodiments, growth factors are delivered to specific regions of the bioreactor using a fiber comprising an outer surface, a hollow core, and a plurality of channels coupling the hollow core to the outer surface. In some embodiments, intestinal growth factors are delivered at selected locations, such as epidermal (EGF), fibroblast (FGF), hepatocyte (HGF), transforming (TGF-β), or insulin-like (IGF) growth factors. Growth factors are signaling proteins that are regulators of the proliferation, differentiation, migration, and survival of cells. In some embodiments, the growth factors are introduced using microfluidic conduits or channels coupled to a hollow core. In some embodiments, the fiber comprising a hollow core is coupled to a pump to deliver the growth factors. In some embodiments, peristaltic motion may be generated along the entire gut model using shape memory alloy actuation technology.

In some embodiments, growth factors are introduced by nanofluidic methods using a hollow fiber with a porous membrane and a piezoelectric control for the delivery of very small volumes into the gut. The aforementioned growth factors are commercially available.

Fibers are thermally drawn from 3D printed multimaterial rods called preforms. During the process, the cross-sectional geometries are preserved. The functionality of the fiber is determined by the material selection. The fiber can be further developed by thermally initiating capillary breakup of its core to create arrays of spheres used for specific functions. The fibers technology CELLINK Bio X can support extensions that allow the fiber to be fed through the bioink during a print. This also requires a new design of nozzles that can be precisely printed in biocompatible resin.

FIGS. 5A-C shows an overview of fiber technology in gut bioreactors. FIG. 5A shows fibers are fed through the print head nozzle with bioink as the base for the 3-D construct of the reactor. FIG. 5B shows the flow of microorganisms (Q) through the gut volume (V) with embedded fibers in the encoded villi (Φ). FIG. 5C shows the biofunctional and biosensing fibers being drawn at high temperature from a rod composed of a variety of functional materials. During the draw process, the cross-sectional area of the rod or preform will be preserved, allowing for radial arrangement control of the fiber. Using a post-processing method initiating capillary instability in the core of the fiber by controlled heat, the axial direction can be manipulated to transformed linear cores into periodic spheres. Using micro- and nano-fiber technology allows the generation of measurements with high temporal and spatial resolution so that various models can be tested model predictions about the metabolism and functioning of whole-gut bioreactors. Specifically, building on results in 3D control of internal fiber architecture (Gumennik et al. 2013, Gumennik et al. 2017), allows the development of artificial microvasculature and innervation fabric embedding ultrasonic microtransducer-based biosensors that will coat the interior of the gut bioreactor to map biofilm formation ultrasonically. The incorporation of the fiber-based devices allows for a better understanding of the cellular microenvironment. The length and time scales of interaction between cells and microrganisms, and between neighboring cells are biologically relevant. Such a microenvironment allows the cells to interact with neighboring organisms, form their own extracellular matrix, and respond to the surrounding stimuli in a non-artificial environment. This is unlike bioreactors where tissue specific cells are bioprinted on inert materials. The gut model interior can be inlayed with sensors for monitoring changes in $CO_2$, pH, and $O_2$ (Zhu et al. 2015). This can be accomplished by incorporating a GFP-labeled human embryonic kidney cell line (HEK293) cells into the bioink, which in combination with direct physiological measurement will allow the validation of biofunctional and biosensing capabilities.

CAD Design and Computational Simulations

Using computer-aided design (CAD), a digital model that captures the microscale complexity of the mammalian gut. Small and large folds that are lined with rows of offset villi have been generated. These folds and villi are coiled around a cylinder of intestinal volume to mimic the spiral shape of the mucosa in the GI tract. Next, CAD models and encoding for biofilm production. Simulations can be run with different villi sizes based on patient data.

In some embodiments, theoretical average residence time can be calculated by dividing the volume of a given system by the flow rate of that system. In some embodiments, this theoretical residence time would be the residence time of a pulse of particles in a plug-flow style system where all particles that enter at the same time exit at the same time due to the nature of the fluid flow in the reactor. In complex reactors, residence time is a distribution of times that particles exit a system as fluid flow is complex and dead zones emerge. The distribution of residence times in these systems can be determined using tracers that are added to the system at a given time. Timed fractions of the system outflow may be collected and the tracer is quantified in each fraction allowing a residence time distribution to be calculated from the concentration curve generated.

In some embodiments, the bioreactor is configured to provide a realistic architecture of mammalian intestine morphology varying in size (but not limited to) from the mice to a human. A based asymmetrical structure of crypts and villus as a foundation and added variable controls of its shape (the folds) and components (the villi) were modeled to find patterns in microbial residence over time in the gut. The bioreactor described herein is capable of being scaled up or down to fit various animal guts having similar morphology. In one embodiment, stereolithography was used to generate various models with a precision of 50 micrometers in various biocompatible materials.

Most materials available to rapid prototyping that are biocompatible tend to be rigid. In some embodiments, an elastic material that preserves the designed features was used to print the bioreactor. In some embodiments, the bioreactor comprises materials that may be sterilized allowing the bioreactor to be reused for different experiments. In some embodiments, the bioreactor comprises an outer shell and the internal bioreactor comprises a soft gel material that may be single use.

Printing Fibers for Sensing and Supporting a Bioreactor

In one embodiment, the fibers in FIG. 5C may be produced using the same methods according to the methods disclosed in the cross-referenced application titled "VERY LARGE SCALE INTEGRATION FOR FIBERS (VLSI-Fi)". In the first stage, a preform is composed of different materials. The various geometry shown in FIG. 5C can be achieved by 3D printing or milling the preforms and then consolidating them together in an oven at a selected temperature under vacuum. In addition, the bars of material can be hot pressed together. In the second stage, the preform is vertically inserted in a furnace. Under the weight of gravity and additional weight at the end of the rod, as the temperature increases across the rod, the rod begins to elongate and form a fiber. In some embodiments, the thermal drawn fiber may elongate over meter-to-kilometer distances. This process may be done using a draw tower that spans over multiple floors in a bay area. In the third stage, segments of the fiber are cut and go through post-processing steps to characterize the fiber and give it functions. For example, one can control the thickness of the outer dimension through chemical etching. Other examples include breaking up an internal core into an array of consecutive spherical droplets due to capillary instabilities initiated if the fiber undergoes further heat treatment configured to melt the internal core and surrounding cladding of the fiber.

Figure 17:
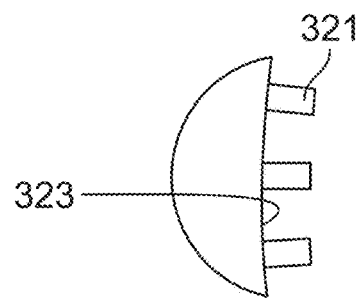
FIG. 17 is an enlarged view of FIG. 15.

In some embodiments, one or more multimaterial fibers may be incorporated into the bioreactor. Based on the bioreactor material, the fiber may be incorporated during the printing process of the bioreactor, wherein a soft material is used to form the bioreactor. Referring to FIG. 17, in some embodiments, the bioreactor is 3D printed to include one or more channels for inserting the multi-material fiber into the bioreactor. The channels transverse the body of the bioreactor and have an inlet and an outlet. The inlet couples to the internal region of the bioreactor (referred to as the reactor region) and the outlet couples to the outer surface of the bioreactor allowing the multi-material fiber to protrude from the bioreactor and couple to a device that sends and receives information.

In one embodiment, a microfluidic fiber is formed comprising a hollow core channel and periodic outlets to delivery or retrieve fluids. The fiber may be made out of a biocompatible polymer such as polycarbonate. Briefly, a method of fabrication/activation comprises 1) a preform is 3D printed with a central core, and one or more thin hollow core midway between the outside of the fiber and the core channel, 2) the fiber is drawn, 3) capillary breakup is conducted to break the one or more thin cores into spheres, 4) an etching agent (for example acetone if the fiber is made out of polycarbonate) is used to open up the spheres and the large central channel, and 5) the end of the fiber is hooked to a peristaltic or syringe pump to control the delivery of fluids.

In one embodiment, a nanofluidic delivery system comprises piezoelectric material, electrodes, and a porous membrane. Briefly, a method of fabrication and activation comprises 1) a preform is printed with a specific internal arrangement to house functional material, 2) two-material heterogeneous gel is introduced to the porous membrane location, 3) if the electrodes and piezoelectric materials melt at high temperatures, they will be introduced in the form of wires during the drawing process—otherwise, they are simply placed in the desired locations in the hollow core of the preform, 4) the fiber is drawn with all its materials, 5) an etching agent is used to selectively remove one of the two materials present in the porous gel to create the porosity, 6) electrodes are hooked to a power generator and a reservoir to control the flow through the fiber. This fiber is used to control pico amounts of fluid flowing into the bioreactor—for example delivery a specific fluid to a prespecified crypt.

In one embodiment, a fiber to mimic peristaltic actuation in the bowel movement of the gut is provided. Briefly, a method of fabrication/activation comprises 1) a preform is printed with the desired geometry including core cavities, 2) shape memory polymers or alloys are introduced into the core cavities, 3) the fiber is drawn, 4) the shape memory material of the fiber is connected to a function generator at the end of the fiber to control its motion.

In one embodiment, a fiber to sense density growth of cells, for example bacteria, is provided. Briefly, a method of fabrication/activation comprises 1) a preform is printed with the desired geometry, 2) electrodes and piezoelectric material is inserted in the fiber, 3) the fiber is drawn, 4) capillary breakup is applied to form the internal devices and the electrodes are exposed at the end of the fiber, and 5) the fiber's electrodes are connected to a function generator to send signals through the device and another fiber's electrodes are hooked to an oscilloscope or LCR meter to observe the output signal and disturbances in the system.

In one embodiment, a fiber to sense stress levels in the environment is provided. Briefly, a method of fabrication/activation comprises 1) a preform is printed with the desired geometry, 2) electrodes and piezoelectric material is inserted in the fiber, 3) the fiber is drawn, 4) capillary breakup is applied, and 5) the electrodes of the fiber are hooked to an oscilloscope or LCR meter to identify stress levels.

The one or more multi-material fibers may be simultaneously printed with the 3D printed material or they may be inserted post printing using predefined channels.

Incorporating the Fibers into the Bioreactor

In one embodiment, in a first step, the gut model is made out of a biocompatible resin, enabling analysis over a fixed and controlled biomimicry realization of the natural process. This serves as a static analysis of the biosystem. In some embodiments, in a second step, the gut model is made out of bioink, a lab-produced alternative to the natural ECM that supports cell and bacterial organization, adhesion, proliferation, and their biological behavior. The bioink is designed to match the material properties of the ECM. In some embodiments, the bioink may be composed of biodegradable synthetic polymers, such as poly(glycolicacid) (PGA), poly(lacticacid) (PLA), poly(lactide-co-glycolide), polyanhydride, poly(propylenefumarate), polycaprolactone (PCL), polyethyleneglycol (PEG), polyurethane, or a combination thereof. In some embodiments, the bioink may be composed of naturally-sourced biopolymers such as proteins polysaccharides, or a combination thereof. In some embodiments, the proteins may include collagen, gelatin, silk, fibrin, or a combination thereof. In some embodiments, the polysaccharides may include alginates, agarose, chitosan, glycosaminoglycans, or combinations thereof. In some embodiments, the ECM may comprise synthetic and inorganic bioceramics, such as calcium phosphates, tricalcium phosphates, hydroxyapatite, bioglass, or combinations thereof, each of which may be inert, resorbable, or degradable.

In some embodiments, a soft gut model may be provided. With a soft gut model, actuation can be introduced to model the peristaltic motion using shape-memory alloys and polymers. In this embodiment, a platform for a dynamic analysis of the biosystem is provided.

Hard or rubber-like components of the bioreactor may be printed individually and then assembled (i.e., Commercial SLA resins by Formlabs). That is because the printed method used, stereolithography does not allow for any external interference during the printing process. In some embodiments, stereolithography may be used because of the high precision printing output. FIG. 17 shows how channels may be formed in the bioreactor to enable the introduction of multi-material fibers.

In some embodiments, gel-based soft material devices can be extruded along with the one or more multi-material fibers due to the printing technology used in bioprinting that allows custom-made nozzles to be inserted. For example, a nozzle capable of being autoclaved comprising resin may be used having two inputs, one for the printing material and one for the one or more multi-material fibers. The material and the one or more multi-material fibers combine at a single extruding point from the printer nozzle so as to form the bioreactor with the one more or more fibers incorporated.

In terms of the fiber's introduction into the device, one end of surface (along the fiber) can interact with the biological environment (i.e., the reactor region) while the other end of the fiber is either connected to an electronic generator and/or measurement device, or the fiber is connected to a source of fluids. Such connections are well established in the field of microfluidics of lab-on-chips technology for example.

Using the conduits/channels or the placement of the fibers during printing, the one or more multi-material fibers may interact directly with the biofilm and the bioreactor environment. The one or more fibers are designed to be biocompatible.

In some embodiments, the one or more fibers or woven into the bioreactor by additive manufacturing. In the bioreactor, the fibers are incorporated within the wall volume or at the wall internal surface of the gut model, depending on the fiber functionality. In some embodiments, these fibers may be used for biostimuli and biosensing modalities, such as ultrasound imaging, shape tracking, peristaltic motion, bio-chemical delivery, surface morphology biomimetics (microvilli) and so forth. To that end, custom printheads that enable an efficient incorporation of the fiber into the printing material is provided. Here, the solutions grade by complexity that is correlated to the optimization of such integration. In one embodiment, a fiber is dipped manually into the bioink at the beginning of its extrusion and spooled of by the shear stress applied by the surrounding bioink. The spool is set on a bearing allowing it to rotate with very low friction. These embodiments involve coating the fiber in bioink introduced at specific locations using rollers and a pneumatic feed. In one embodiment, this is done in a biosafety chamber of the printer. Therefore, the print-head add-ons are designed to resist the exposure to UV.

Figure 7:
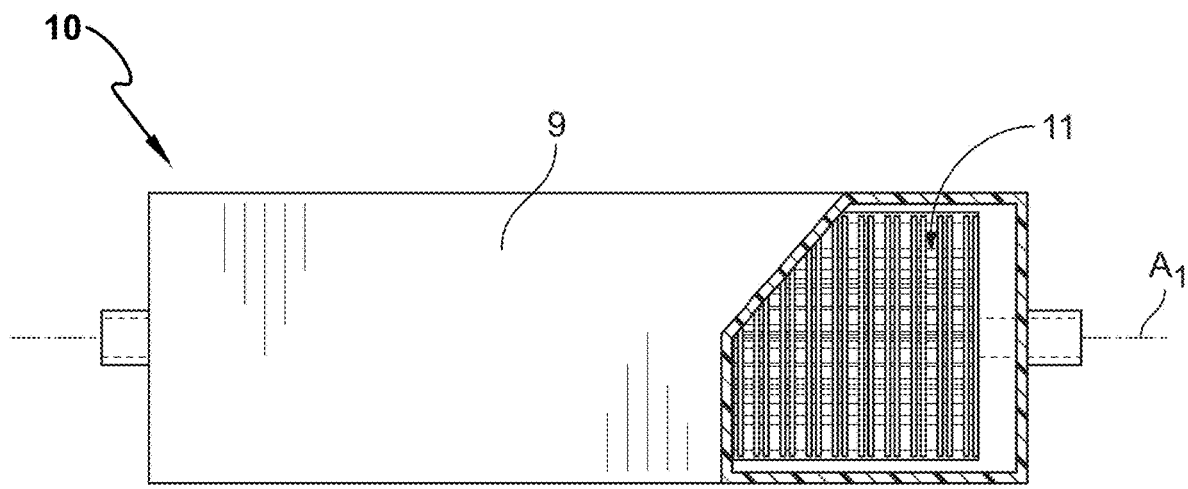
FIG. 7 is a perspective view of a gut bioreactor.

FIG. 7 is a perspective view of a gut bioreactor 10 according to the present disclosure. The gut bioreactor 10 is generally cylindrical and extends around a central axis A1 that extends through the center of the gut bioreactor 10. The gut bioreactor 10 includes a housing 9 and FIG. 7 shows a portion of the housing 9 broken away. The gut bioreactor 10 is formed to include reactor region that includes a fold region 14 and a flow region 12. The gut bioreactor 10 may include an inlet and outlet that are configured to pass fluid through the gut bioreactor.

Figure 8:
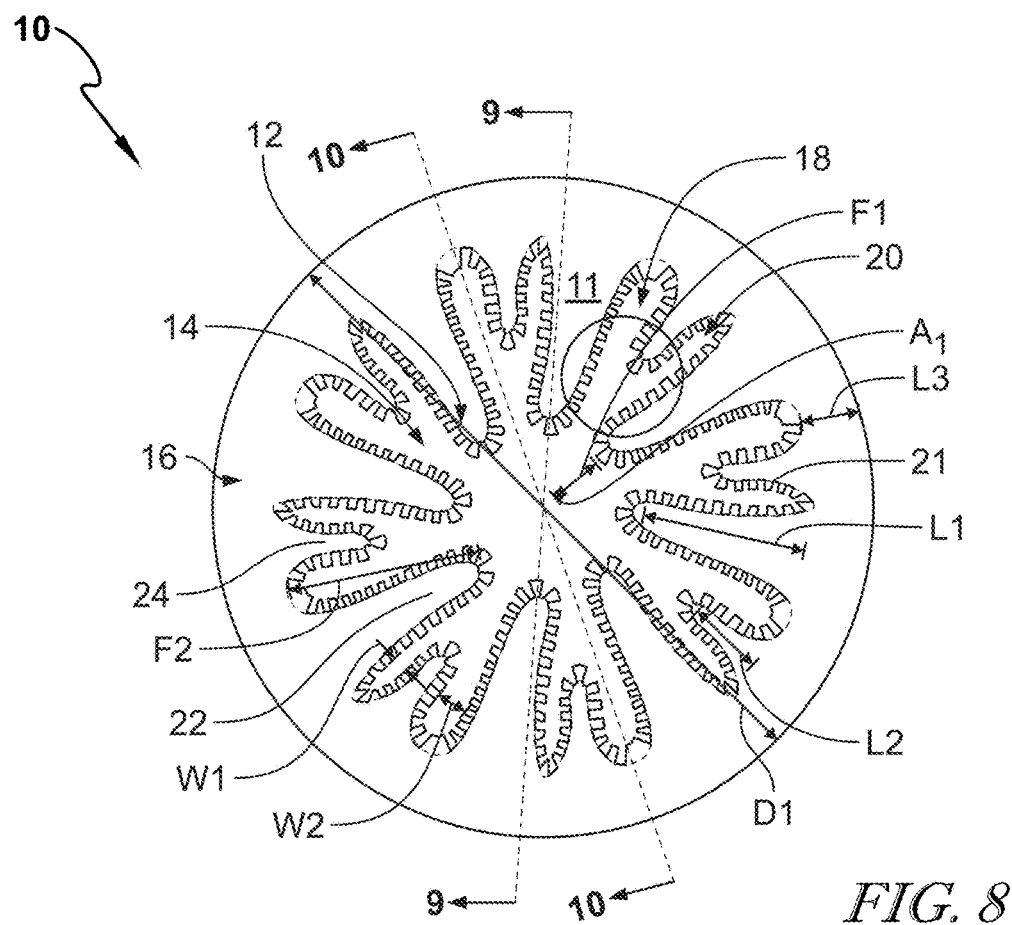
FIG. 8 is an overhead view of the gut bioreactor of FIG. 7.
Figure 9:
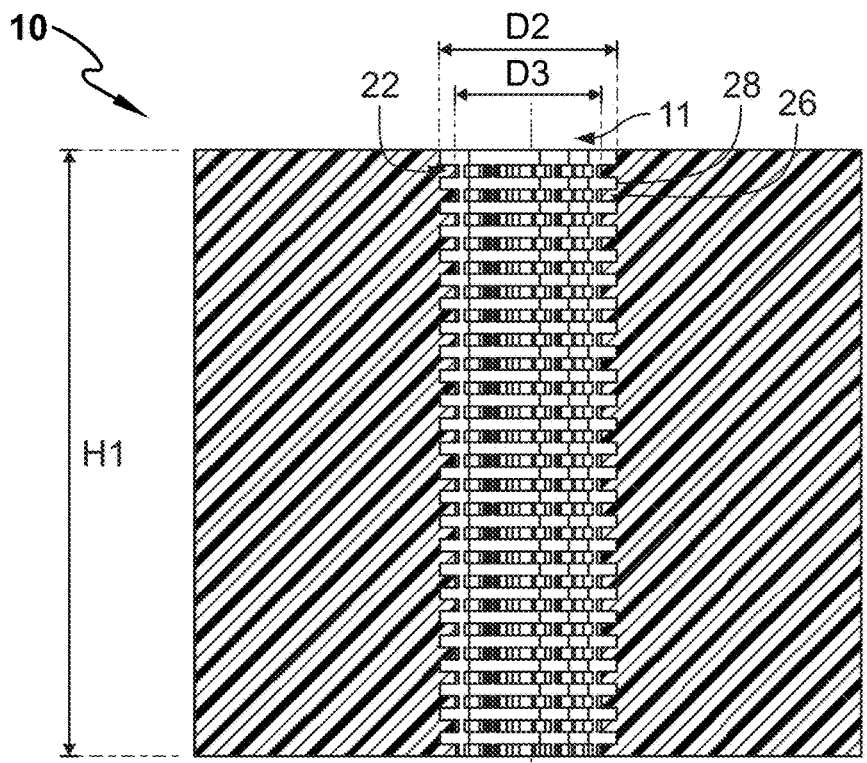
FIG. 9 is a sectional view taken along line 9-9 of FIG. 8.

The gut bioreactor 10 has a height H1 as shown in FIG. 9. In some embodiments, H1 is about 10 cm to about 30 cm although H1 may determined according to the end use of the gut bioreactor 10. The gut bioreactor 10 also has a diameter D1 as shown in FIG. 8. In some embodiments, D1 is about 0.50 cm to about 4.0 cm although D1 may be determined according to the end use of the gut bioreactor 10. In some embodiments, the gut bioreactor 10 also has a diameter D2 and D3, wherein D2 is larger than D3 as shown in FIG. 9. In some embodiments, D2 is at least about 0.01 cm in length.

In some embodiments, D2 is about 0.01 cm to about 2 cm. In some embodiments, D3 is at least 0.005 cm in length. In some embodiments, D3 is about 0.005 cm to about 1.95 cm.

FIG. 8 is an overhead view of the gut bioreactor 10 from FIG. 7. The gut bioreactor 10 includes the flow region 12, the fold region 14, and an outer ring 16. The flow region 12 extends outwardly from the central axis a distance of F1. The outer ring 16 is arranged to surround the flow region 12 and the fold region 14. The fold region 14 extends between and interconnects the flow region 12 and the outer ring 16. Illustratively, the fold region 14 extends outwardly toward the outer ring 16 from the flow region a distance F2.

Figure 10:
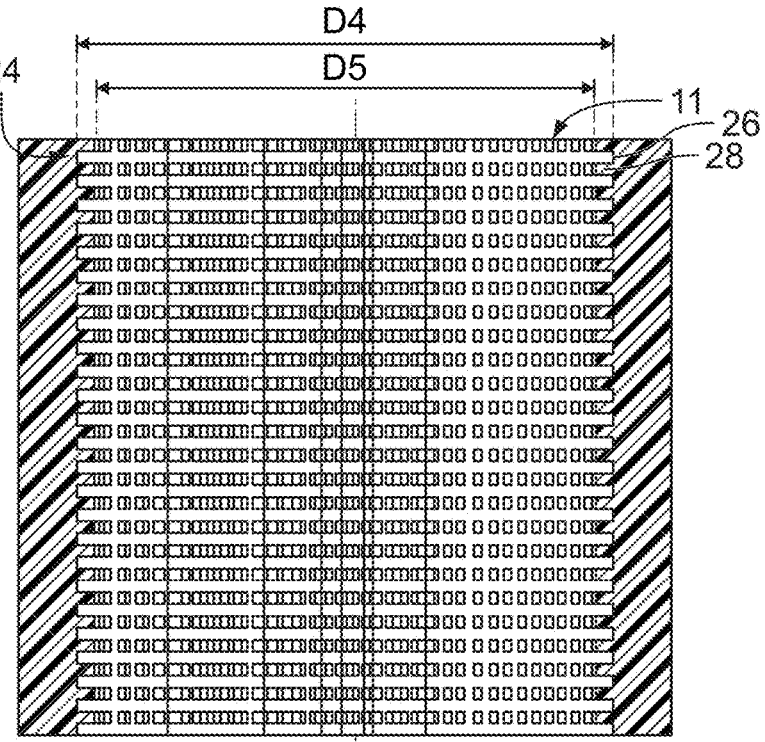
FIG. 10 is a sectional view taken along line 10-10 of FIG. 8.

Referring to FIG. 10 in some embodiments, the gut bioreactor 10 includes a diameter D4 and diameter D5, wherein D4 is larger than D5. In some embodiments, D4 is at least 0.50 cm in length. In some embodiments, D4 is about 1.0 cm to about 4.0 cm. In some embodiments, D5 is at least 0.25 cm in length. In some embodiments, D5 is about 0.25 cm to about 3.95 cm in length.

The gut bioreactor 10 includes a member 22 and a member 24, as shown in FIG. 8. Member 22 extends into the reactor region 11 a distance L1. Member 22 is formed to include a plurality of protuberances 21 that extend from a surface of member 22 into the reactor region 11. Member 24 is located spaced apart from member 22. Member 24 extends into the reactor region 11 a distance L2. Member 24 is formed to include a plurality of protuberances 21 that extend from a surface of member 24 into the reactor region 11. Illustratively, L1 is greater than L2. In some illustrative embodiments, members 22 and 24 cooperate to form crypt regions, as discussed below.

Illustratively, the gut bioreactor includes several members 22 and members 24 located around the central axis A1 and extending into the reactor region 11. The members 22, 24 cooperate to form the fold structures discussed below. As shown in FIGS. 9 and 10. The diameter D3 as measured between two members 22 is less than the diameter D5 between members 24 that are across the central axis A1.

Referring to FIG. 9, FIG. 10, FIG. 12, and FIG. 14, in illustrative embodiments, the gut bioreactor 10 includes several fold regions 14 that extend around the central A1. In some embodiments, the gut bioreactor 10 includes eight fold regions 14. It should be understood that the number of fold regions can be adjusted depending on the end use and the gut being modeled. For example, a gut bioreactor 10 may include 2-14 fold regions.

Illustratively, the gut bioreactor 10 is formed of a plurality of reactor plates 26 and spacer plates 28. The reactor plates 26 include the members 22, 24 as discussed above and the protuberances 21. In some embodiments, the reactor plates 26 align so that the members 22, 24 overlie one another. In some embodiments, the reactor plates 26 are slightly offset so that the members 22, 24 from adjacent reactor plates are offset. Illustratively, offset reactor plates 26 form a spiral structure. The spacer plates 28 are generally devoid of protuberances and operate to separate the reactor plates 26. The diameter D2 is a diameter of the spacer plate near member 22. Diameter D4 is a dimeter of the spacer plate near member 24. D2 is generally less than D4.

The fold region 14 includes a crypt region 18, as shown in FIG. 8. In some embodiments, fold region 14 includes two crypt regions 18, 20. In illustrative embodiments, the crypt regions 18, 20 are sized differently, as shown in FIG. 8. Illustratively, each fold region may include a major crypt region 18 and a minor crypt region 20. In some embodiments, the major crypt region 18 has a diameter W2 of about 0.76 cm or at least 0.76 cm. In some embodiments, the minor crypt region 20 has a diameter W1 of about 1.52 cm or at least 1.52 cm. In some embodiments, the diameter of the crypt region between each fold is about 2.29 cm. In some embodiments, the gut bioreactor 10 includes eight fold regions.

Figure 11:
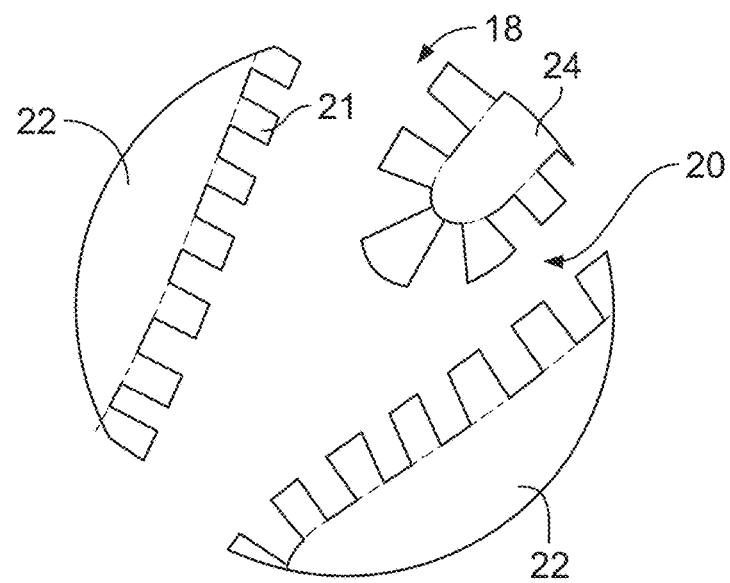
FIG. 11 is an enlarged view of a portion of FIG. 8.

Referring to FIG. 11, member 24 is located between two members 22. Member 24 may be equally spaced between the two members 22 or may be nearer than one. In illustrative embodiments where member 24 is not centered, the fold region can form two crypt regions having different sizes, as discussed below.

In some embodiments, the reactor region 11 has an average diameter of about 1.50 cm to about 4.5 cm. In some embodiments, the average diameter of the reactor region 11 is about 1.50 cm, about 1.55 cm, about 1.60 cm, about 1.65 cm, about 1.70 cm, about 1.75 cm, about 1.80 cm, about 1.85 cm, about 1.90 cm, about 1.95 cm, or about 2.0 cm. In some embodiments, the average diameter of the reactor region 11 is about 2.0 cm, about 2.25 cm, about 2.50 cm, about 2.75 cm, about 3.0 cm, about 3.25 cm, about 3.50 cm, about 3.75 cm, about 4.0 cm, about 4.25 cm, or about 4.50 cm. In some embodiments, the reactor region 11 diameter is about 1.71 cm.

In some embodiments, the villi or protuberances 21 are located at regular intervals of about 0.127 cm along the length of the fold region 14. In one embodiment, the fold region 14 may comprise about 200 to 350 villi (i.e., protuberances 21). In one embodiment, the fold region 14 comprises 296 villi (i.e., protuberances 21) having a length extending into the reactor region 11 of about 0.38 mm to about 0.75 mm. In some embodiments, the protuberances 21 have a generally uniform size and distribution. In some embodiments, the protuberances 21 vary in length between about 0.25 mm to about 0.99 mm.

The bioreactor 10 may comprise biocompatible materials. In some embodiments, the bioreactor 10 comprises plastic, resin, rubber, glass, or a combination thereof. In some embodiments, the bioreactor 10 is 3D printed using stereolithographic resins such as Dental SG, Dental LT, gelatin methacrylate having flexible, durable, and elastic properties, a UV curable hydrogel, a plastic such as polycarbonate, glass, or a combination thereof.

In some embodiments, a peristaltic pump is coupled to the bioreactor 10. The pump is configured to pass liquid through the gut bioreactor 10. In some embodiments, the fluid flows through the inlet and outlet of the housing. In some embodiments, the pump is coupled with the multimaterial fibers and passes fluid through the multimaterial fibers. Illustratively, this mimics peristalsis in a mammalian gut. In some embodiments, the pump is configured to pass fluid through the flow region 12 and/or the fold region 14.

Figure 12:
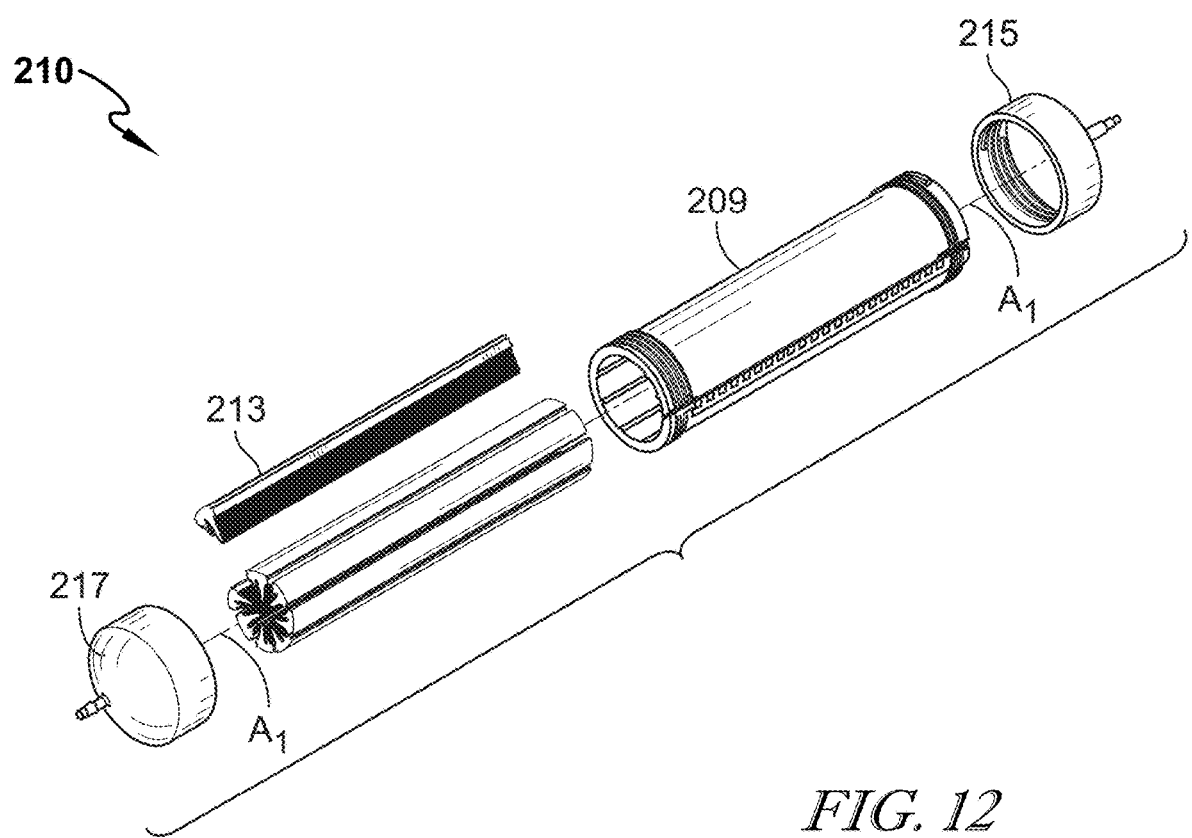
FIG. 12 is an exploded assembly view of another embodiment of a gut bioreactor.

FIG. 12 is another embodiment of a gut bioreactor 210. The gut bioreactor 210 includes two caps 215, 217 that couple with a reactor housing 209. Gut bioreactor 210 is formed of a several reactor strips 213 that extend around a central axis A1. The reactor strips 213 combine to form the series of reactor plates 226 and spacer plates 228 as discussed above for the gut bioreactor 210.

Figure 13:
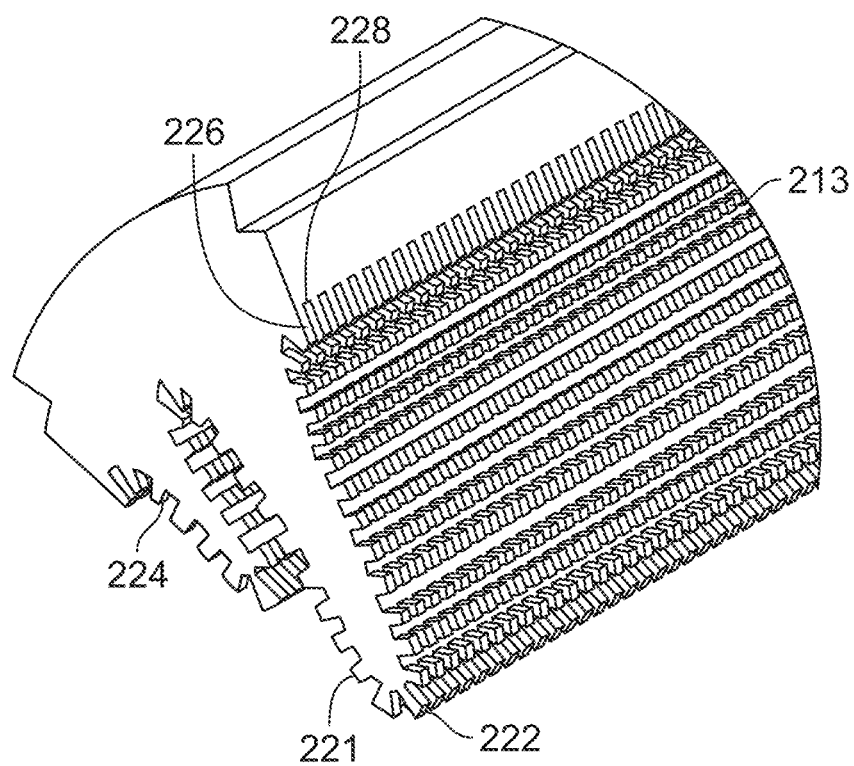
FIG. 13 is a perspective view of a reactor strip of the gut bioreactor of FIG. 12.
Figure 14:
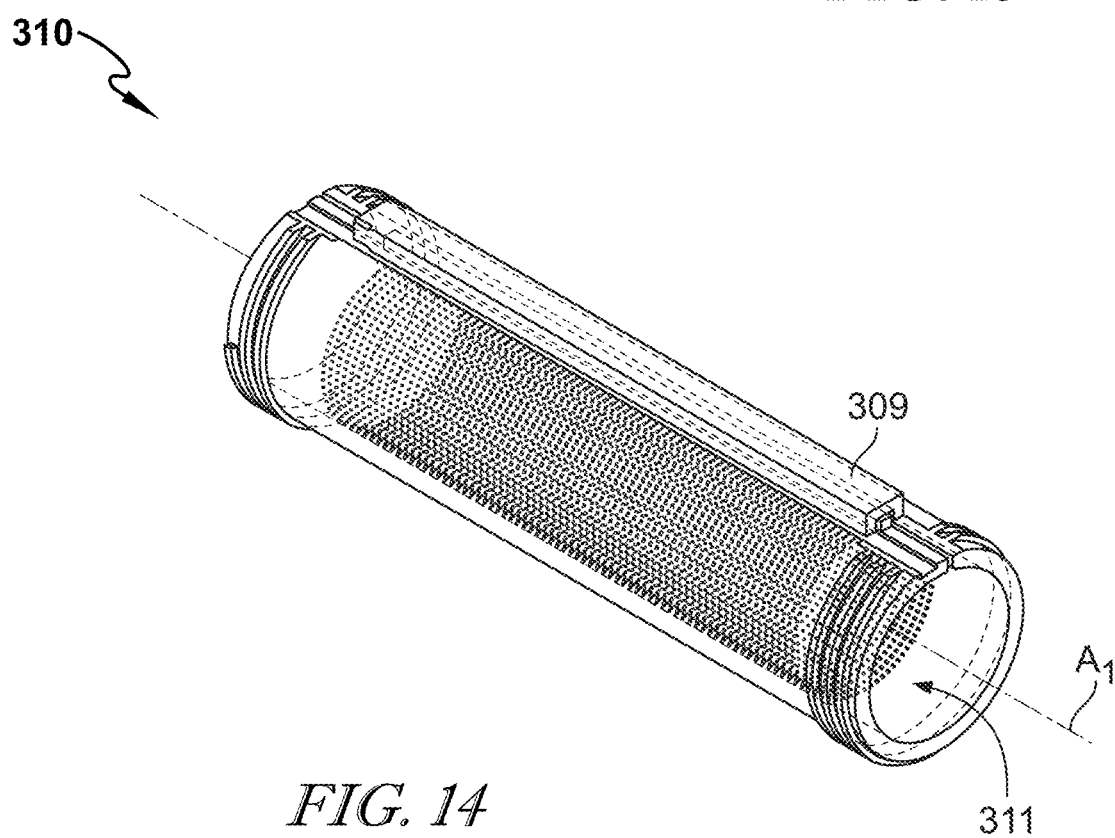
FIG. 14 is a perspective view of another embodiment of a gut bioreactor.
Figure 15:
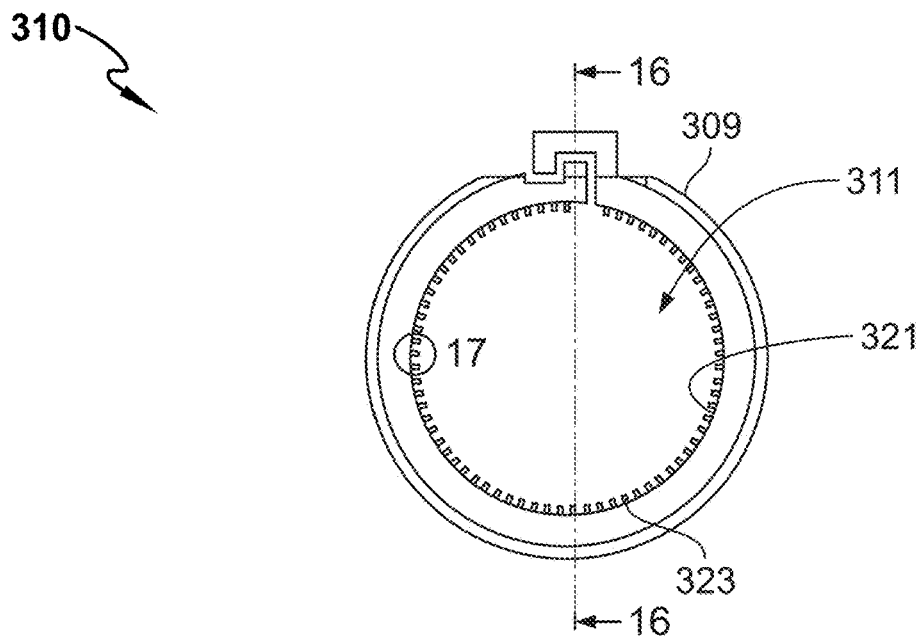
FIG. 15 is an overhead view of the gut bioreactor of FIG. 14.
Figure 16:
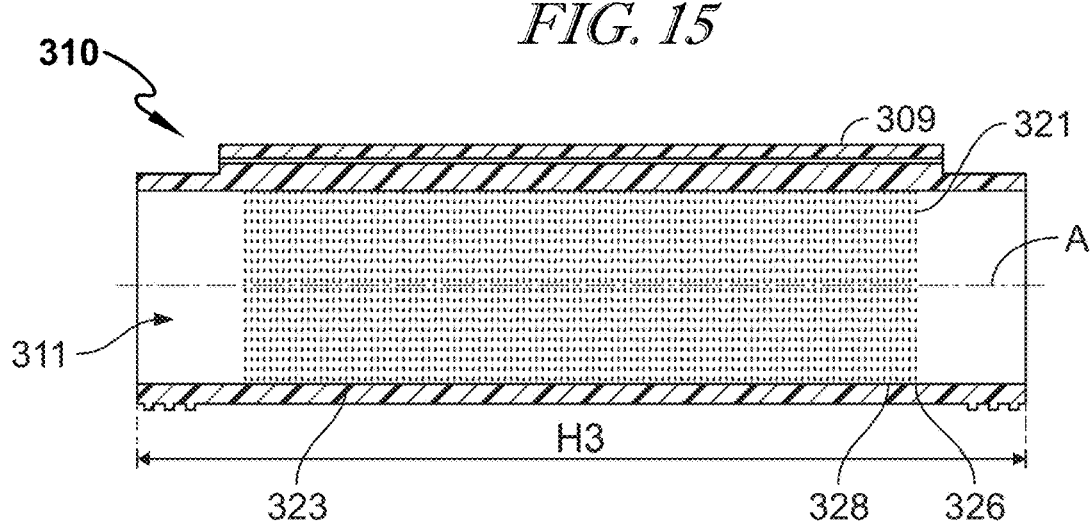
FIG. 16 is a sectional view taken along line 16-16 of FIG. 15.

Referring now to FIG. 13, each reactor strip 213 includes a member 222 and a member 224. The above disclosure regarding members 22 and 24 are incorporated by reference here. Each of the members 222, 224 are formed to include a plurality of protuberances 221.

Referring now to FIG. 14-17, a gut bioreactor 310 includes a housing 309 that is formed to include a reactor region 311 therein. Unlike the gut bioreactors 10, 210, the gut bioreactor 310 does not include members extending into the reactor region 311. Instead, the protuberances 321 extend into the reactor region 311 from an inner sidewall 323. The gut bioreactor 310 includes a plurality of reactor plates 326 and spacer plates 328.

Figure 18:
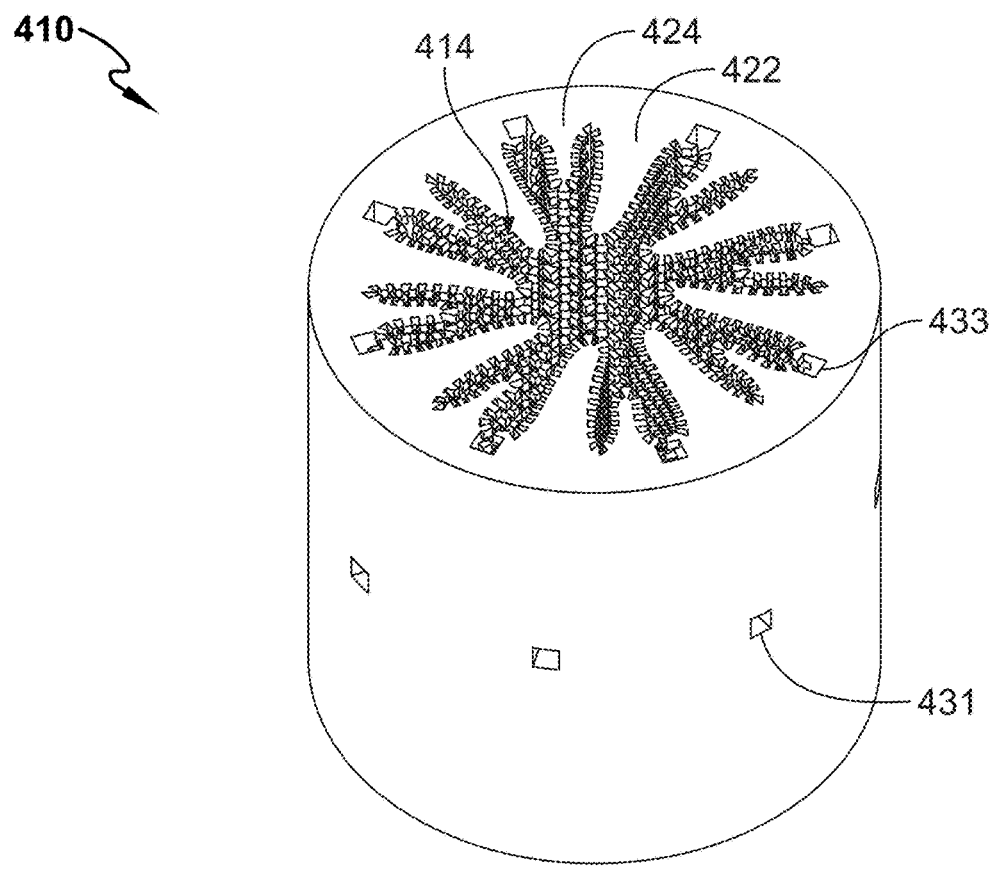
FIG. 18 is a perspective view of a gut bioreactor including openings for a multimaterial fiber.
Figure 19:
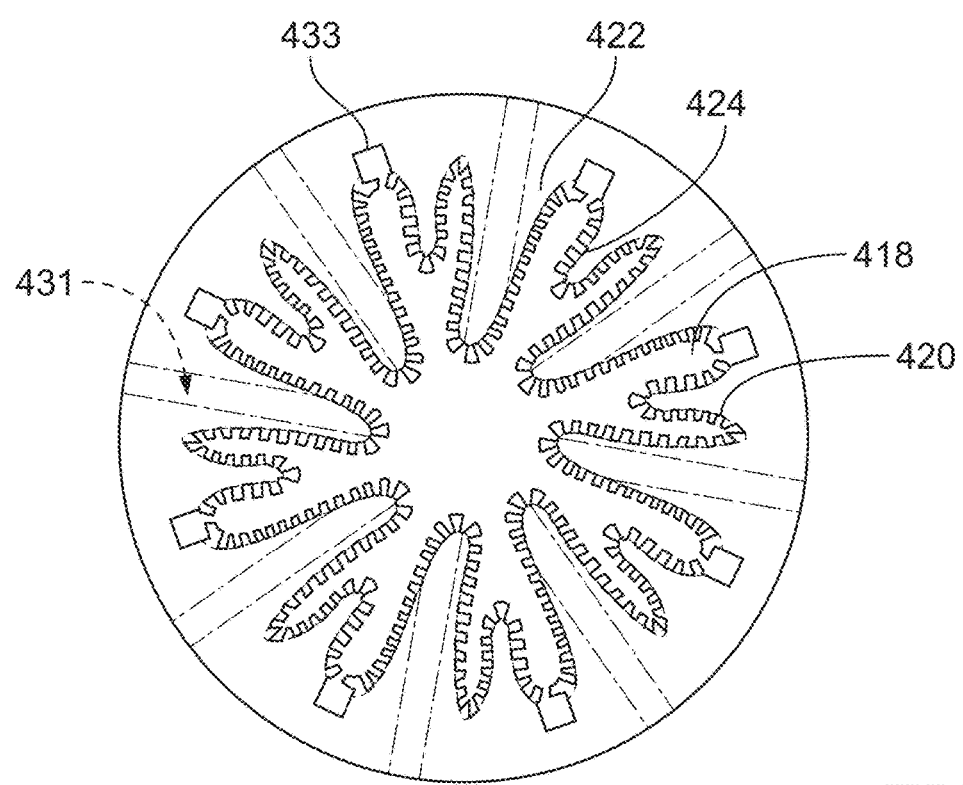
FIG. 19 is an overhead view of the gut bioreactor of FIG. 18.

Referring now to FIGS. 18 and 19, a gut bioreactor 410 resembles the gut bioreactor 10. Illustratively, the gut bioreactor 410 includes members 422 and 424. The above disclosure regarding members 22 and 24 are incorporated by reference here. The members 422 and 424 cooperate to form the crypts 418 and 420. Illustratively, the crypt 418 is larger than crypt 420 but alternative embodiments have the crypts of similar size. The crypt 418 is formed to include a conduit 433 that allows a multimaterial fiber to pass therethrough and to the outlet 431. As viewed from above, the conduit 433 is square however the shape may be adjusted depending on the shape of the multimaterial fiber passed therethrough. Although FIGS. 18 and 19 show the conduit 433 in only one crypt per fold region 414, any number of conduits are available depending on the number and types of multimaterial fibers. Also, the conduit 433 is drawn at the base of the crypt 420 but may be located anywhere along the members 422, 424.

Figure 20:
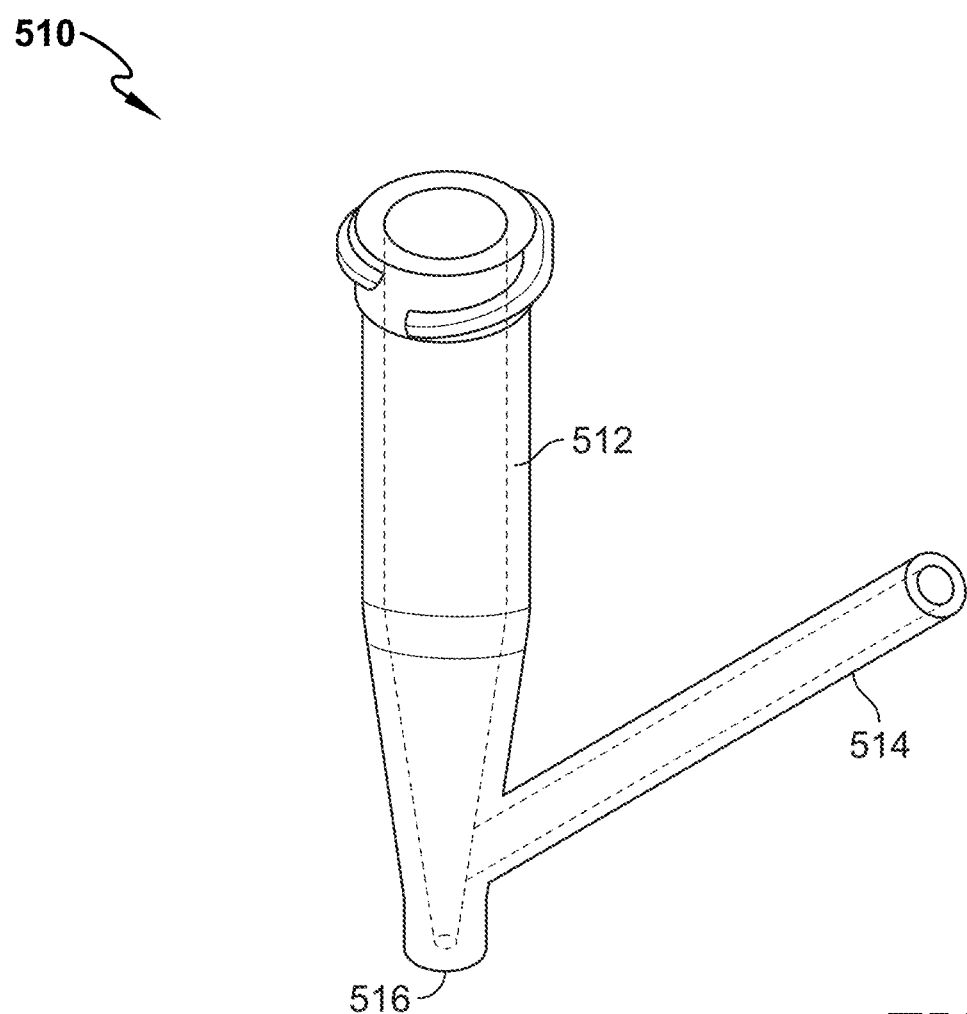
FIG. 20 is a perspective view of a nozzle for use in printing gut bioreactors comprising multimaterial fibers.
Figure 21:
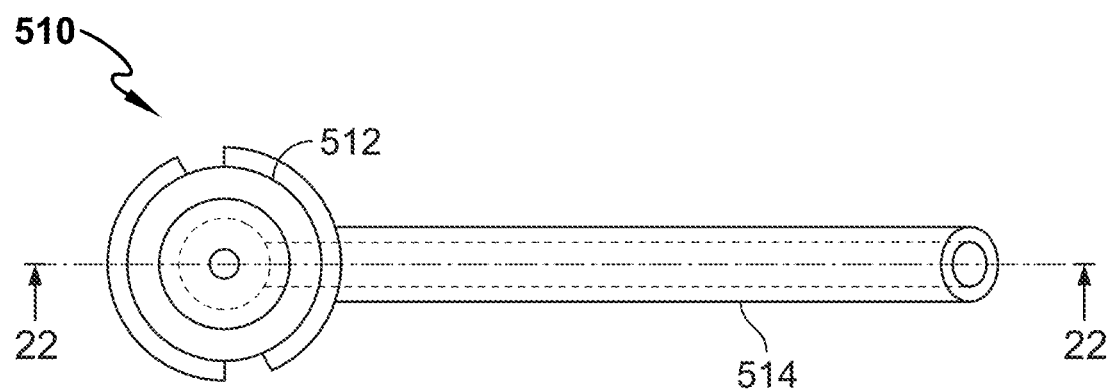
FIG. 21 is an overhead view of the nozzle of FIG. 20.
Figure 22:
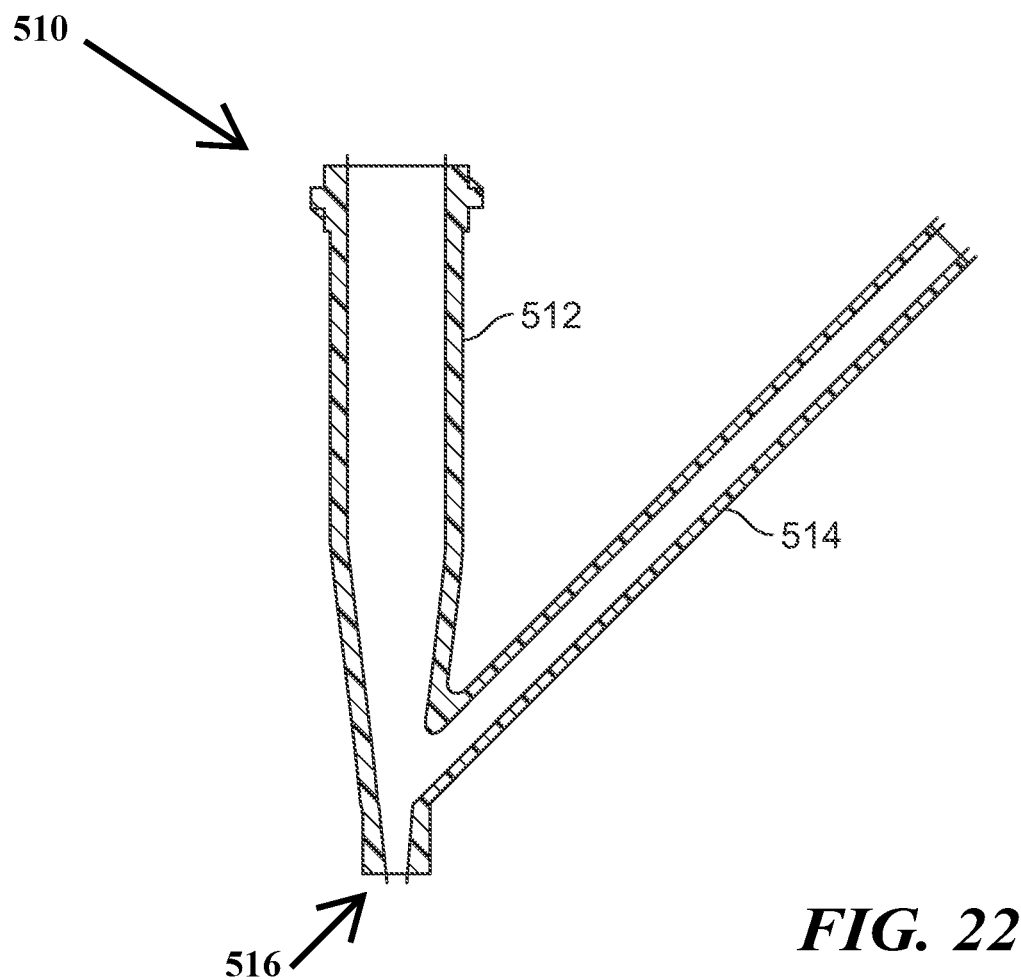
FIG. 22 is a sectional view taken along line 22-22 of FIG. 21.

Referring now to FIGS. 20-22, a nozzle 510 for forming the gut bioreactors 10, 210, 310, 410 is shown. The nozzle 510 includes a body 512 and a body 514. The matrix for forming the solid portions of the gut bioreactors 10, 210, 310, 410 is passed through the body 512. The multimaterial fibers described herein pass through the body 514. At the junction where the bodies 512, and 514 meet, the fiber becomes coated with the matrix and it exits the outlet 516 to be printed. In some embodiments, the nozzle 510 is formed of a polypropylene.

The following embodiments are also contemplated.

Clause 1. A method of forming a bioreactor, comprising: printing fiber preforms, drawing fiber preforms, coating drawn fibers with bioink, wherein the bioink contains an ECM, assembling the drawn fibers into a structure having a receptacle surrounded by (i) at least one inner wall surface and (ii) at least one outer wall surface.

Clause 2. The method of clause 1, wherein the fiber preforms are polycarbonate.

Clause 3. The method of clause 1, wherein the fiber preforms are multi-material.

Clause 4. The method of clause 1, wherein the fibers are capable of biosensing metabolites.

Clause 5. The method of clause 1, wherein the fibers are capable of biosensing growth factors.

Clause 6. The method of clause 1, wherein the fibers are capable of biostimulating cells.

Clause 7. The method of clause 1, wherein the one inner wall surface includes undulations.

Clause 8. The method of clause 1, wherein the undulations on the inner wall resemble villi.

Clause 9. The method of clause 8, wherein the undulations on the inner wall resemble crypts.

Clause 10. A bioreactor, comprising: a receptacle surrounded by a wall having an inner wall surface and an outer wall surface, wherein (i) the wall is made of fibers coated with bioink and (ii) the bioink contains ECM.

Clause 11. The bioreactor of clause 10, wherein the fiber preforms are polycarbonate.

Clause 12. The bioreactor of clause 10, wherein the fiber preforms are multi-material.

Clause 13. The bioreactor of clause 10, wherein the fibers are capable of biosensing metabolites.

Clause 14. The bioreactor of clause 10, wherein the fibers are capable of biosensing growth factors.

Clause 15. The bioreactor of clause 10, wherein the fibers are capable of biosensing residence time.

Clause 16. The bioreactor of clause 10, wherein the fibers are capable of biostimulating cells.

Clause 17. The bioreactor of clause 10, wherein the bioink contains ECM and cells.

Clause 18. The bioreactor of clause 10, wherein the inner wall surface includes undulations.

Clause 19. The bioreactor of clause 18 wherein the undulations on the inner wall resemble villi.

Clause 20. The bioreactor of clause 18, wherein the undulations on the inner wall resemble crypts.

Clause 21. A method of modeling a gut microbiome system, comprising: providing a set of parameters associated with physical and geometrical properties of a gut microbiome system, programing the set of parameters into an IBM, generating a computational simulation of the gut microbiome system based upon the set of parameters, wherein the simulation includes a prediction of a trait of the gut microbiome system, providing a 3D-printed gut bioreactor, wherein the 3D-printed gut bioreactor is configured to possess the same set of parameters associated with the physical and geometrical properties as those programed into the IBM, conducting an experiment utilizing the 3D-printed gut reactor to generate data that describes an actual trait of the microbiome system, and comparing the characteristics of the predicted trait to the characteristics of the actual trait.

Clause 22. The method of clause 21, wherein the predicted trait includes the trait of how the gut microbiome reacts to a biologically active compound.

Clause 23. The method of clause 21, wherein the predicted trait includes a trait of a diseased gut microbiome.

Clause 24. A method of modeling a gut microbiome system, comprising: providing a set of parameters associated with physical and geometrical properties of a gut microbiome system, programing the set of parameters into an IBM, generating a computational simulation of the gut microbiome system based upon the set of parameters, wherein (i) the simulation includes a prediction of a trait of the gut microbiome system and (ii) the predicted trait includes the trait of how the gut microbiome reacts to a biologically active compound.

Clause 25. A method of modeling a gut microbiome system, comprising: providing a set of parameters associated with physical and geometrical properties of a gut microbiome system, programing the set of parameters into an IBM, generating a computational simulation of the gut microbiome system based upon the set of parameters, wherein (i) the simulation includes a prediction of a trait of the gut microbiome system and (ii) the predicted trait includes a trait of a diseased gut microbiome.

Clause 26. A method of modeling a gut microbiome system, comprising: providing a set of parameters associated with physical and geometrical properties of a gut microbiome system, programing the set of parameters into an IBM, generating a computational simulation of the gut microbiome system based upon the set of parameters, wherein (i) the simulation includes a prediction of a trait of the gut microbiome system and (ii) the predicted trait includes a trait of how a diseased gut microbiome reacts to a biologically active compound.

Clause 27. A system for studying a microbiome, comprising a 3D bioreactor, wherein the 3D bioreactor embedded with biosensing fibers includes epithelial cells.

Clause 28. The system of clause 27, wherein the epithelial cells are human epithelial cells.

Clause 29. The system of clause 27, wherein the biosensing fibers are capable of measuring the amounts of metabolites.

Clause 30. The system of clause 27, wherein the 3D bioreactor includes a biofilm.

Clause 31. The system of clause 27, wherein the 3D bioreactor includes villi.

Clause 32. The system of clause 27, wherein the 3D bioreactor includes cell spheroids.

Clause 33. The system of clause 27, wherein the spheroids include intestinal smooth muscle cells and intestinal epithelial cells.

Clause 34. The system of clause 33, wherein the spheroids form crypts.

Clause 35. The system of clause 27, wherein the 3D bioreactor includes GFP-labeled human embryonic kidney cell line (HEK 293).

Clause 36. A system for studying a microbiome, comprising a 3D bioreactor, wherein the 3D bioreactor includes cells incorporated into a gel.

All references, including publications, patent applications, patents, and code cited herein are hereby incorporated by reference to the same extent as if each reference were individually and specifically indicated to be incorporated by reference and were set forth in its entirety herein.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A bioreactor comprising:
   a cylindrical body comprising a biocompatible material formed to include a reactor region therein,
   a first member extending into the reactor region a first distance, the first member formed to include a plurality of protuberances that extend from a surface of the first member into the reactor region, and
   a second member located spaced apart from the first member and extending into the reactor region a second distance that is generally less than the first distance of the first member, the second member formed to include a plurality of protuberances that extend from a surface of the second member into the reactor region;
   wherein the first member and the second member cooperate to form a first crypt region located between a portion of the protuberances from the first member and a portion of the protuberances of the second member, and
   wherein a multimaterial fiber extends through the body.

2. The bioreactor of claim 1, comprising a third member located spaced apart from the first member to locate the second member therebetween, wherein the third member extends into the reactor region a third distance and the third member is formed to include a plurality of protuberances that extend from a surface of the third member into the reactor region.

3. The bioreactor of claim 2, wherein the first distance and the third distance are the same.

4. The bioreactor of claim 3, wherein the second member and the third member cooperate to form a second crypt region located between a portion of the protuberances from the second member and a portion of the protuberances of the third member.

5. The bioreactor of claim 4, wherein the first crypt has a width D1 as measured by the distance between protuberances of the first member and the second member and the second crypt has a width D2 as measured by the distance between the protuberances of the second member and the third member, and D1 and D2 are different.

6. The bioreactor of claim 1, wherein the body comprises plastic, resin, rubber, glass, or a combination thereof.

7. The bioreactor of claim 1, wherein the body comprises bioink including extracellular matrix and cells.

8. The bioreactor of claim 1, wherein the multimaterial fiber is located between a base of the first member and a base of the second member.

9. The bioreactor of claim 1, wherein the multimaterial fiber is configured to detect at least one of pH, $CO_2$, $O_2$, cell density, environmental stress, or temperature.

10. The bioreactor of claim 1, wherein the multimaterial fiber is configured to enable peristaltic motion or microfluidic control.

11. The bioreactor of claim 1, wherein the protuberances on the first member are evenly spaced apart from one another.

12. The bioreactor of claim 1, wherein the protuberances on the first member are not evenly spaced apart from one another.

13. The bioreactor of claim 1, comprising a fold region formed to include the second member and at least a portion of the first member and a portion of the third member.

14. A bioreactor comprising:
   a cylindrical body comprising a biocompatible material formed to include a reactor region therein,
   a first member extending into the reactor region a first distance, the first member formed to include a plurality of protuberances that extend from a surface of the first member into the reactor region,
   a second member located spaced apart from the first member and extending into the reactor region a second distance that is generally less than the first distance of the first member, the second member formed to include a plurality of protuberances that extend from a surface of the second member into the reactor region; and
   a fold region formed to include the second member and at least a portion of the first member and a portion of the third member;
   wherein the bioreactor comprises a plurality of fold regions that extend around a central axis so that a distal end of a first member of a first fold region and a distal end of a first member of a second fold member located opposite the first fold member across the central axis define a flow channel; and
   wherein the first member and the second member cooperate to form a first crypt region located between a portion of the protuberances from the first member and a portion of the protuberances of the second member.

* * * * *